(12) United States Patent
Li et al.

(10) Patent No.: US 8,685,719 B2
(45) Date of Patent: *Apr. 1, 2014

(54) POLYNUCLEOTIDE CONSTRUCTS FOR INCREASED LYSINE PRODUCTION

(75) Inventors: Lhing-Yew Li, Savoy, IL (US); Kelli J. Trei, Decatur, IL (US)

(73) Assignee: Archer Daniels Midland Company, Decatur, IL (US)

( * ) Notice: Subject to any disclaimer, the term of this patent is extended or adjusted under 35 U.S.C. 154(b) by 104 days.

This patent is subject to a terminal disclaimer.

(21) Appl. No.: 11/510,084

(22) Filed: Aug. 25, 2006

(65) Prior Publication Data

US 2006/0286645 A1 Dec. 21, 2006

Related U.S. Application Data

(63) Continuation of application No. 10/067,974, filed on Feb. 8, 2002, now Pat. No. 7,368,276, and a continuation of application No. 09/722,441, filed on Nov. 28, 2000, now Pat. No. 6,927,046.

(60) Provisional application No. 60/267,183, filed on Feb. 8, 2001, provisional application No. 60/184,130, filed on Feb. 22, 2000, provisional application No. 60/173,707, filed on Dec. 30, 1999.

(51) Int. Cl.
*C12N 15/00* (2006.01)

(52) U.S. Cl.
USPC ........................................ 435/320.1

(58) Field of Classification Search
None
See application file for complete search history.

(56) References Cited

U.S. PATENT DOCUMENTS

| | | | |
|---|---|---|---|
| 3,959,075 A * | 5/1976 | Inuzuka et al. ............... | 435/115 |
| 4,346,170 A | 8/1982 | Sano et al. | |
| 4,411,997 A | 10/1983 | Shimazaki et al. | |
| 4,514,502 A | 4/1985 | Miwa et al. | |
| 4,559,308 A | 12/1985 | Nutter et al. | |
| 4,601,983 A | 7/1986 | Nakamori et al. | |
| 4,710,471 A | 12/1987 | Katsumata et al. | |
| 4,757,009 A | 7/1988 | Sano et al. | |
| 4,778,762 A | 10/1988 | Miwa et al. | |
| 4,822,738 A | 4/1989 | Miwa et al. | |
| 4,861,722 A | 8/1989 | Sano et al. | |
| 4,954,441 A | 9/1990 | Katsumata et al. | |
| 5,158,891 A | 10/1992 | Takeda et al. | |
| 5,236,831 A | 8/1993 | Katsumata et al. | |
| 5,243,039 A | 9/1993 | Schendel et al. | |
| 5,380,657 A | 1/1995 | Schaefer et al. | |
| 5,426,050 A | 6/1995 | Morinaga et al. | |
| 5,426,052 A | 6/1995 | Flickinger et al. | |
| 5,547,864 A | 8/1996 | Kawasaki et al. | |
| 5,591,577 A | 1/1997 | Tsuchiya et al. | |
| 5,597,727 A | 1/1997 | Kohama et al. | |
| 5,633,154 A | 5/1997 | Schaefer et al. | |
| 5,643,790 A | 7/1997 | Morinaga et al. | |
| 5,661,012 A | 8/1997 | Sano et al. | |
| 5,688,671 A * | 11/1997 | Sugimoto et al. ............. | 435/115 |
| 5,693,781 A | 12/1997 | Zupancic et al. | |
| 5,700,661 A | 12/1997 | Katsumata et al. | |
| 5,726,299 A | 3/1998 | Zupancic et al. | |
| 5,766,925 A | 6/1998 | Sugimoto et al. | |
| 5,804,414 A | 9/1998 | Moriya et al. | |
| 5,876,983 A | 3/1999 | Sugimoto et al. | |
| 5,929,221 A | 7/1999 | Kimura et al. | |
| 5,965,391 A | 10/1999 | Reinscheid et al. | |
| 5,989,875 A | 11/1999 | Kojima et al. | |
| 6,004,773 A | 12/1999 | Araki et al. | |
| 6,027,920 A | 2/2000 | Joliff et al. | |
| 6,037,154 A | 3/2000 | Suga et al. | |
| 6,040,160 A | 3/2000 | Kojima et al. | |
| 6,090,597 A | 7/2000 | Hirano et al. | |
| 6,200,785 B1 | 3/2001 | Kreutzer et al. | |
| 6,221,636 B1 | 4/2001 | Hayakawa et al. | |
| 6,927,046 B1 * | 8/2005 | Hanke et al. ................. | 435/106 |
| 8,067,210 B2 * | 11/2011 | Hanke et al. ................. | 435/106 |

FOREIGN PATENT DOCUMENTS

| | | |
|---|---|---|
| EP | 0 387 527 A | 9/1990 |
| EP | 0 733 710 A | 9/1996 |
| EP | 0 754 756 | 1/1997 |
| EP | 0 841 395 A | 5/1998 |
| EP | 0 854 189 | 7/1998 |
| EP | 857 784 A2 | 8/1998 |
| EP | 1 108 790 | 6/2001 |
| WO | WO 96/34961 | 11/1996 |
| WO | WO 01/49854 A2 | 7/2001 |

OTHER PUBLICATIONS

Scott et al., Nat. Genet. 21:440-443, 1999.*
Eggeling et al., Naturwissenschaftern 86:33-38, 1999.*
Scapin et al., Biochemistry 35:13540-13551, 1996.*
Cremer, J. et al., "Control of the Lysine Biosynthesis Seq. in *Corynebacterium glutamicum* as Analyzed by Overexpression of the Ind. Corresponding Genes," Appl. Environ. M crobiol. 57:1746-1752, Americon Society for Microbiology (1991).
Malumbres, M., & Martin, J.F., "Molecular control mechanism of lysine & Threonine biosynthesis n amino acid-prod corynebacteria: Redirecting carbon flow," FEMS Lett. 145:103-114, Elsevier Science B.V. (1996).
Marcel, T.et al., "Nucleotide sequence & organization of the upstream region of the *Corynebacterium glutamicum* lysA gene," Mol. Microbiol. 4:1819-1830, Blackwell Scientific Publications (1990).

(Continued)

*Primary Examiner* — David J Steadman
(74) *Attorney, Agent, or Firm* — Mark W. Roberts

(57) ABSTRACT

The invention relates to production of lysine, and provides several isolated polynucleotide molecules useful for the production of L-lysine. One such polynucleotide encodes an aspartate kinase (ask), an aspartate-semialdehyde dehydrogenase (asd) and a dihydrodipicolinate reductase (dapB). Other polypeptides encode ask, asd, dapB and a diaminopimelate dehydrogenase (ddh); ask, asd, dapB, ddh and an ORF2 poypeptide; and ask, asd dapB, ddh, ORF2 and a diaminopimelate decarboxylase (lysA). The invention further provides methods of making and using the polynucleotides, and methods to increase the production of L-lysine.

1 Claim, 21 Drawing Sheets

(56) References Cited

OTHER PUBLICATIONS

Jobling, M.G., & Holmes, R.K., "Construction of vectors with the p15a replicon, kanamycin resistance, inducible lacZa & pUC18 or or pUC19 multiple cloning site," Nucl. Acids Res. 18:5315-5316, IRL Press (1990).

Kleeman, A., etal., "Amino Acids," in Ullmann's Encylopedia of Ind. Chemistry, 5th, Completely Rev. Ed., vol. A2: Amines, Aliphatic to Antibiotics, Gerhartz, W., ed., VCH Verlagsgesellschaft mbH, Weinheim,Germany, pp. 57-97 (1985).

Lonsdale, D.M., et al., "pFC1 to pFC7: A Novel Family of Compinatorial Cloning Vectors," Plant Mol. Biol. Report, 13:343-345, Transaction Periodicals Consortium, Rutgers University (1995).

Archer, J.A.C. & Sinskey, A.J., "The DNA sequence & minimal replicon of the *Corynebacterium glutamicum* plasmid pSR1: evidence of a common ancestry with plasmids from *C. diphtheriae*," J. Gen. Microbiol. 139:1753-1759, The Soc. for Gen. Microb. (1993).

Ben-Samoun,K. et al., "Positively regulated expression of the *Escherichia coli* araBAD promoter in *Corynebacterium glutamicum*" FEMS Microbiol. Lett. 174:125-130, Elsevier Science B.V. (1999).

Chatterjee,M. & Chatterjee, S.P., "Microbial Prod. of L-lysine: A Review," Hind. Antibiot. Bull. 39:20-49, Hindustan Antibiotics Ltd. (1997).

Correia, A.et al., "Cloning & characterization of an IS-like element present in the genome of *Brevibacterium lactofermentum* ATCC 13869," Gene 170:91-94, Elsevier Science (1996).

Cremer, J. et al., "Regulation of Enzymes of Lysine Biosynthesis in *Corynebacterium glutamicum*," J. Gen. Microbiol. 134:3221-3229, Society for General Microbiology (1988).

Anonymous, "Advances in the Biotechnology of Lysine Production," Nutr. Rev. 43:88-90, International Life Sciences Institute (1985).

Bannur, B.B., & Purandare, G.M., "Microbial Production of L-lysine," Hind. Antibiot. Bull. 11:191-205, Hindustan Antibiotics Ltd. (1969).

Batt,C.A.et al., "Genetic engineering of coryneform bacteria," Trends Biotechnol. 3:305-310, Elsevier Science Publishers (1985).

Huang,H.T., "Microbial Production of Amino Acids," in Progress in Industrial Microbiology (vol. 5), Hockenhull, D.J.D., ed., Gordon & Breach Science Publishers, Great Britain, pp. 57-92 (1964).

Ishino,S. et al., "Cloning & Sequencing of the meso-Diaminopimelate-D-dehydrogenase (ddh) Gene of *Corynebacterium glutamicum*," Agric. Biol. Chem. 52:2903-2909, The Agricultural Chemical Society of Japan (1988).

Jetten, M.S.M. et al., "Metabolic Engineering of *Corynebacterium glutamicum*," Ann. NY Acad. Sci 721:12-29, The New York Academy of Sciences (1994).

Follettie, M. & Sinskey, A.J., "*Corynebacterium glutamicum*: A Model for the llse of DNA Tech. in Food Grade Organisms," in Biotechnology & Food Safety, Bills, D.D. & Kung, S.D., eds., Butterworth-Heinemann, Boston, MA, pp. 277-289 (1990).

Follettie, M.T., et al., "Gene Structure & Expression of the *Corynebacterium flavum* N13 ask-asd Operon," J. Bacteriol. 175:4096-4103, The Am. Soc. for Microbiology (1993).

Frankard, V., et al., "Molecular characterization of an *Arabidopsis thaliana* cDNA coding for a monofunctional aspartate kinase," Plant Mol. Bio. 34:233-242, Kluwer Academic Publishers (1997).

Schwarzer, A., & Puhler, A., "Manipulation of *Corynebacterium glutamicum* by Gene Disruption & Replacement," Biotechnology 9:84-87, Nature PUblishing Co. (1991).

Selli, A. et al., "Regulation of Dihydrodipicolinate Synthase & Diaminopimelate Decarboxylase Activity in *Bacillus stearothermophilus*," Ital. J. Biochem. 43:29-35, II Pensiero Scientifico (1994).

Shiio, I. et al., "Isolation and properties of Lysine-Producing Mutants with Feedback-resistant Aspartokinase Derived from a *Brevibacterium flavum* Strain with Citrate Synthase-& Pyruvate Kinase-defects & Feedback-resistant Phosphoenolpyruvate Carboxylase," Agric. Biol. Chem. 54:3275-3282, Japan Soc. for Bioscience, Biotechnology, & Agrochemistry (1990).

Shilo, I. et al., "Isolation & Properties of a-Ketobutyrate-resistant Lysine-producing Mutants from *Brevibacterium flavum*" Bioscl. Biotech. Biochem. 57:51-55, Japan Soc. for Bioscience, Biotechnology, & Agrochemistry (1993).

Sonnen, H. et al., "Characterization of pGA1, a new plasmid from *Corynebacterium glutamicum* LP-6," Gene 107:69-74, Elsevier Science Publishers (1991).

Stragier,P. et al., "Regulation of Diaminopimelate Decarboxylase Synthesis in *Escherichia coli*," J.Mol. Biol. 168:321-331 Academic Press (1983).

Yeh,P. et al., "General organization of the genes specifically involved in the diaminopimelate-lysine biosynthetic pathway of *Corynebacterium glutamicum*," Mol. Gen. Genet. 212:105-111, Springer-Verlag (1988).

Yoshihama, M. et al., "Cloning Vector System for *Corynebacterium glutamicum*," J. Bacteriol. 162:591-597, American Society for Microbiology (1985).

Marcel,T. et al., "Nucleotide sequence & organization of the upstream region of the *Corynebacterium glutamicum* lysA gene," Mol. Microbiol. 4:1819-1830, Blackwell Scientific Publications (1990).

Nakayama, K. et al., "Microbial Production of Essential Amino Acids with *Corynebacterium glutamicum* Mutants," in Nutritional Improvement of Food & Feed Proteins, Freidman, M., ed., Plenum Press, NY, NY, pp. 649-661 (1977).

Cremer, J. et al., "Cloning the dapA dapB cluster of the lysine-secreting bacterium *Corynebacterium glutamicum*," Mol. Gen. Genet. 220:478-480, Springer-Verlag (1990).

Eikmanns, B.J. et al., "Amplification of three threonine biosynthesis genes in *Corynebacterium glutamicum* & its influence on carbon flux in different strains," Appl. Microbiol. Biotechnol. 34:617-622, Springer-Verlag (1991).

Eikmanns, B.J. et al., "Molecular aspects of lysine, threonine, & isoleucine biosynthesis in *Corynebacterium glutamicum*," Antonie van Leeuwenhoek 64:145-163, Kluwer Academic Publishers (1993).

Jetten, M.S.M., et al., "Effect of different levels of aspartokinase on the lysine production by *Corynebacterium lactofermentum*," Appl. Microbiol. Biotechnol. 43:76-82, Springer-Verlag (1995).

Jetten, M.S.M., & Sinskey, A.J., "Recent Advances in the Physiology & Genetics of Amino Acid-Producing Bacteria," Crit. Rev. Biotechnol. 15:73-103, CRC Press (1995).

Kalinowski, J.et al., "Aspartokinase genes lysCa & lysCB overlap & are adjacent to the aspartate B-semialdehyde dehydrogenase gene asd in *Corynebacterium glutamicum*," Mol. Gen. Genet. 224:317-324, Springer-Verlag (1990).

Kalinowski, J. et al., "Genetic & biochemical analysis of the aspartokinase from *Corynebacterium glutamicum*," Mol. Microbiol. 5:1197-1204, Blackwell Scientific Publications (1991).

Kinoshita, S. et al., "L-Lysine Production Using Microbial Auxotroph," J. Gen. Appl. Microbiol. 4:128-129, The Institute of Applied Microbiology (1958).

Liebl,W., et al., "Transfer of *Brevibacterium divaricatum* DSM 2097[T], "*Brevibacterium flavum*" DSM 20411, *Brevibacterium lactofermentum*" DSM 20412 & DSM 1412, & *Corynebacterium lilium*.

DSM 20137 to *Corynebacterium glutamicum* and Their Distinction by rRNA Gene Restriction Patterns, Int. J. Syst. Bacteriol. 41:255-260, Int'l. Union of Microbiological Socities (1991).

Wendisch, V.F., et al., "Regulation of acetate metabolism in *Corynebacterium glutamicum*: transcriptional control of the isocitrate lyase & malate synthase genes," Arch. Microbiol. 168:262-269, Springer-Verlag (1997).

Database EMBL Acc. No. Z21502, Pisabarro, A., et al. (Aug. 16, 1993).

Database EMBL Acc. No. AX122246, Nakagawa, S., et al. (May 11, 2001).

Database EMBL Acc. No. AX123535, Nakagawa, S., et al. (May 11, 2001).

Database EMBL Acc. No. AX125746, Nakagawa, S., et al. (May 10, 2001).

Pisabarro A. et al., "A cluster of Three Genes (DAPA, ORF2, & DAPB) of *Brevibacterium lactofermentum* Encodes Dihydrodipicolinate Synthase, Dihydrodinicolinate Reductase & a

(56) References Cited

OTHER PUBLICATIONS

Third Polypetide of Unknown Function," May 1, 1993 pp. 2743-2749, vol. 175,No. 9,Journal of Bacteriology, Wash, DC, USA.
Jetten MSM et al., "Effect of Different Levels of Aspartokinase on lysine production by *Corynebacterium lactofermentum*," 1995, pp. 76-82, vol. 43, No. 1, Applied Microbiology & Biotechnology, Springer-Verlag, Berlin, Germany.
"Introduction to Protein Structure", Branden & Tooze, Garland Publishing INc., New York, 1991, p. 247.
Witkowski et al. (1999) Biochemistry 38:11643-11650.
Guo et al. Proc. Natl. Acad. Sci. 101: 9205-9210, 2004.
Marcel,T.et al., "Nucleoties sequence & organization of the upstream region of the *Corynebacterium glutamicum* lysA gene," Mol. Microbiol. 4:1819-1830, Blackwell Scientific Publications (1990).
Oguiza,J.A. et al., "A Gene Encoding Arginyl-tRNA Synthetase Is Located in the Upstream Region of the lysA Gene in *Brevibacterium lactofermentum*: Regulation of argS-lysA Cluster Expression by Arginine," J. Bacteriol. 175:7358-7362, Am. Soc. for Microbiology (1993).
Patek,M. et al., "Promoters from *Corynebacterium glutamicum*: cloning, molecular analysis & search for a consensus motif," Microbiology 142:1297-1309, The Soc. for Gen. Microbiology (1996).
Pharmingen "pPMG-LIC Bacterial Cloning Vector," in 1999 Research Products Catalog, Pharmingen, San Diego, CA p. 839 (1999).
Record, Jr., M.T. et al., "*Escherichia coli* RNA Polymerase (Eo$^{70}$) Promoters, & the Kinetics of the Steps of Transcription Initiation," in *Escherichia coli* & *Salmonella*, Cellular & Molecular Biology, 2nd Ed., vol. 1 Neidhardt, F.C. et al., eds. ASM Press, Wash., DC, pp. 792-821 (1996).
Reinscheld, D.J., et al., "Cloning, sequence analysis, expression & inactivation of the *Corynebacterium glutamicum* pta-ack operon encoding phosphotransacetylase & acetate kinase," Microbiology 145:503-513, The Soc. for General Microbiology (1999).
Schater,A. et al., "Small mobilizable multi-purpose cloning vectors derived from the *Escherichia coli* plasmids pK18 & pK19: selection of defined deletions in the chromosome of *Corynebacterium glutamicum*," Gene 145:69-73, Elsevier Science B.V. (1994).
Serebrijski, I., et al.,"Multicopy Suppression by asd Gene & Osmotic Stress-Dependent Complementation by Heterologous proA in proA Mutants," J. Bacteriol. 177:7255-7260, A. Soc. for Microbiology (1995).
Serwold-Davis,T.M.et al., "Transformationof *Corynebacterium diphtheriae*, *Corynebacterium ulcerans*, *Corynebacterium glutamicum*, & *Escherichia coli* with the *C. diphtheriae* plasmid pNG2," Proc. Natl. Acad. Sci. USA 84:4964-4968, Nat'l. Academy of Sciences (1987).

Van Walsem, H.J., & Thompson, M.C., Simulated moving bed in the production of lysine, J. Biotechnol. 59:127-132, Elsevier Science B.V. (1997).
Martin, J.F. et al., "Cloning Systems in Amino Acid-Producing Corynebacteria," Biotechnology 5:137-146, Nature Publishing Co. (1987).
Miwa, K., et al., "Construction of L-Threonine Overproducing Strains of *Escherichia coli* K-12 Using Recombinant DNA Techniques" Agric. Biol. Chem. 47:2329-2334, The Agric. Chem. Soc. of JP (1983).
Miwa, K., et al., "Construction of novel shuttle vectors & a cosmid vector for the glutamic acid-producing bacteria *Brevibacterium lactofermentum* & *Corynebacterium glutamicum*," Gene 39:281-286, Elsevier Science Publishers (1985).
Nakayama, K., et al., "Studies on Lysine Fermentation I. The Control Mechanism on Lysine Accumulation by Homoserine & Threonine," J. Gen. Appl. Microbiol. 7:145-154, The Institute of Applied Microbiology (1961).
Nakayama, K. Kinoshita, S., "Studies on Lysine Fermentation II," α, ε-Diaminopimelic Acid and its Decarboxylase in Lysine Producing Strain and Parent Strain, J. Gen. Appl. Microbiol. 7:155-160, The Institute of Applied Microbiology (1961).
Sahm, H. et al., "Construction of L-L sine-, L-Threonine-, or L-lsoleucine-Overproducing Strains of *Corynebacterium glutamicum*," Ann. N.Y. Acad. Sci. 782-25-39, The New York Academy of Sciences (1996).
Sandoval, H. et al., "Screening of plasmids in non-pathogenic corynebacteria," FEMS Microbiol. Lett. 27:93-98, Elsevier Science Publishers (1985).
Schafer, A. et al., "High-Frequency Conjugal Plasmid Transfer from Gram-Negative *Escherichia coli* to Various Gram-Positive Coryneform Bacteria," J. Bacteriol. 172:1663-1666, American Society for Microbiology (1990).
Schrumpf, B., et al., "A Functionally Split Pathway for Lysine Synthesis in *Corynebacterium glutamicum*," J. Bacteriol. 173:4510-4516, Am. Soc. for Microbiology (1991).
Schrumpf, B. et al., "Isolation and prominent characteristics of an L-lysine hyperproducing strain of *Corynebacterium glutamicum*," Appl. Microbiol. Biotechnol. 37:566-571, Springer-Verlag (1992).
Hult et al. Curr. Opin. Biotechnol. 14:395-400, 2003.
Yeh, P., et al., "Nucleotide sequence of the lySA gene of *Corynebacterium glutamicum* & possible mechanisms for modulation of its expression," Mol. Gen. Genet. 212:112-119, Springer-Verlag (1988).
Patek, M. et al., "Identification and transcriptional analysis of the dapB-ORF2-dapA-ORF4 operon of the *Corynebacterium glutamicum*, encoding two enzymes involved in L-lysine syntnesis," Biotechnol. Lett. 19:1113-1117, Chapman Hall (1997).

* cited by examiner

Amino Acid sequence of ATCC 21529 Ask

```
SEQ ID NO: 1     GTGGCCCTGGTCGTACAGAAATATGGCGGTTCCTCGCTTGACAGTGCCGAACGCATTAGA
              1  ------------+------------+------------+------------+------------+------------+  60
SEQ ID NO: 2     M  A  L  V  V  Q  K  Y  G  G  S  S  L  E  S  A  E  R  I  R

AACGTCGCTGAACGGATCGTTGCCACCAAGAAGGCTCGAAATGATGTCGTGGTTGTCTGC
             61  ------------+------------+------------+------------+------------+------------+  120
                 N  V  A  E  R  I  V  A  T  K  K  A  G  N  D  V  V  V  V  C

TCCGCAATGGGAGACACCACGGATGAACTTCTAGAACTTGCAGCGGCAGTGAATCCCGTT
            121  ------------+------------+------------+------------+------------+------------+  180
                 S  A  M  G  D  T  T  D  E  L  L  E  L  A  A  A  V  N  P  V

CCGCCAGCTCGTGAAATGGATATGCTCCTGACTGCTGGTGAGCGTATTTCTAACGCTCTC
            181  ------------+------------+------------+------------+------------+------------+  240
                 P  P  A  R  E  M  D  M  L  L  T  A  G  E  R  I  S  N  A  L

GTCGCCATGGCTATTGAGTCCCTTGGCGCAGAAGCTCAATCTTTCACTGGCTCTCAGGCT
            241  ------------+------------+------------+------------+------------+------------+  300
                 V  A  M  A  I  E  S  L  G  A  E  A  Q  S  F  T  G  S  Q  A

GGTGTGCTCACCACCGAGCGCCACGGAAACGCACGCATTGTTGACGTCACACCGGGTCGT
            301  ------------+------------+------------+------------+------------+------------+  360
                 G  V  L  T  T  E  R  H  G  N  A  R  I  V  D  V  T  P  G  R

GTGCGTGAAGCACTCGATGAGGGCAAGATCTGCATTGTTGCTGGTTTTCAGGGTGTTAAT
            361  ------------+------------+------------+------------+------------+------------+  420
                 V  R  E  A  L  D  E  G  K  I  C  I  V  A  G  F  Q  G  V  N

AAAGAAACCCGCGATGTCACCACGTTGGGTCGTGGTGGTTCTGACACCACTGCAGTTGCG
            421  ------------+------------+------------+------------+------------+------------+  480
                 K  E  T  R  D  V  T  T  L  G  R  G  G  S  D  T  T  A  V  A

TTGGCAGCTGCTTTGAACGCTGATGTGTGTGAGATTTACTCGGACGTTGACGGTGTGTAT
            481  ------------+------------+------------+------------+------------+------------+  540
                 L  A  A  A  L  N  A  D  V  C  E  I  Y  S  D  V  D  G  V  Y

ACCGCTGACCCGCGCATCGTTCCTAATGCACAGAAAGCTGGAAAAGCTCAGCTTCGAAGAA
            541  ------------+------------+------------+------------+------------+------------+  600
                 T  A  D  P  R  I  V  P  N  A  Q  K  L  E  K  L  S  F  E  E

ATGCTGGAACTTGCTGCTGTTGGCTCCAAGATTTTGGTGCTGCGCAGTGTTGAATACGCT
            601  ------------+------------+------------+------------+------------+------------+  660
                 M  L  E  L  A  A  V  G  S  K  I  L  V  L  R  S  V  E  Y  A

CGTGCATTCAATGTGCCACTTCGCGTACGCTCGTCTTATAGTAATGATCCCGGCACTTTG
            661  ------------+------------+------------+------------+------------+------------+  720
                 R  A  F  N  V  P  L  R  V  R  S  S  Y  S  N  D  P  G  T  L

ATTGCCGGCTCTATGGAGGATATTCCTGTGGAAGAAGCAGTCCTTACCGGTGTCGCAACC
            721  ------------+------------+------------+------------+------------+------------+  780
                 I  A  G  S  M  E  D  I  P  V  E  E  A  V  L  T  G  V  A  T

GACAAGTCCGAAGCCAAAGTAACCGTTCTGGGTATTTCCGATAAGCCAGGCGAGGCTGCC
            781  ------------+------------+------------+------------+------------+------------+  840
                 D  K  S  E  A  K  V  T  V  L  G  I  S  D  K  P  G  E  A  A
```

FIG.2A

```
SEQ ID NO: 1        AAGGTTTTCCGTGCGTTGGCTGATGCAGAAATCAACATTGACATGGTTCTGCAGAACGTC
  (CONT.)    841    ------------+------------+------------+------------+------------+  900
SEQ ID NO: 2         K  V  F  R  A  L  A  D  A  E  I  N  I  D  M  V  L  Q  N  V
  (CONT.)

TCCTCTGTGGAAGACGGCACCACCGACATCACGTTCACCTGCCCTCGCGCTGACGGACGC
             901    ------------+------------+------------+------------+------------+  960
                     S  S  V  E  D  G  T  T  D  I  T  F  T  C  P  R  A  D  G  R

CGTGCGATGGAGATCTTGAAGAAGCTTCAGGTTCAGGGCAACTGGACCAATGTGCTTTAC
             961    ------------+------------+------------+------------+------------+ 1020
                     R  A  M  E  I  L  K  K  L  Q  V  Q  G  N  W  T  N  V  L  Y

GACGACCAGGTCGGCAAAGTCTCCCTCGTGGGTGCTGGCATGAAGTCTCACCCAGGTGTT
            1021    ------------+------------+------------+------------+------------+ 1080
                     D  D  Q  V  G  K  V  S  L  V  G  A  G  M  K  S  H  P  G  V

ACCGCAGAGTTCATGGAAGCTCTGCGCGATGTCAACGTGAACATCGAATTGATTTCCATC
            1081    ------------+------------+------------+------------+------------+ 1140
                     T  A  E  F  M  E  A  L  R  D  V  N  V  N  I  E  L  I  S  I

TCTGAGATCCGCATTTCCGTGCTGATCCGTGAAGATGATCTGGATGCTGCTGCACGTGCA
            1141    ------------+------------+------------+------------+------------+ 1200
                     S  E  I  R  I  S  V  L  I  R  E  D  D  L  D  A  A  A  R  A

TTGCATGAGCAGTTCCAGCTGGGCGGCGAAGACGAAGCCGTCGTTTATGCAGGCACCGGA
            1201    ------------+------------+------------+------------+------------+ 1260
                     L  H  E  Q  F  Q  L  G  G  E  D  E  A  V  V  Y  A  G  T  G

CGCTAA
            1261    ------ 1266
                     R  *
```

FIG.2B

Amino Acid sequence of ATCC 21529 asd

SEQ ID NO: 3    ATGAXCACCATCGCAGTTGTTGGTGCAACCGGCCAGGTCGGCCAGGTTATGCGCAGGTTT
                1                                                              60
SEQ ID NO: 4    M  T  T  I  A  V  V  G  A  T  G  Q  V  G  Q  V  M  R  R  F

TTGGAAGAGCGCAATTTCCAGCTGAGACTGTTGGTTTCTTTGCTTCCCCCCGTTCCGCA
                61                                                             120
                L  E  E  R  N  F  P  A  D  T  V  R  F  F  A  S  P  R  S  A

GGCCGTAAGATTGAATTCCGTGGCACGGAAATCGAGGTAGAAGACATTACTCAGGCAACC
                121                                                            180
                G  R  K  I  E  F  R  G  T  E  I  E  V  E  D  I  T  Q  A  T

GAGGACTCCCTCAAGGGCATCGACGTTGCGTTGTTCTCTGCTGGAGGCACCGCTTCCAAG
                181                                                            240
                E  E  S  L  K  G  I  D  V  A  L  F  S  A  G  G  T  A  S  K

CAGTACGCTCCACTGTTTGCTGCTGCAGGCGCGACTGTTGTGGATAACTCTTCTGCTTGG
                241                                                            300
                Q  Y  A  P  L  F  A  A  A  G  A  T  V  V  D  N  S  S  A  W

CGCAACGACGACGAGGTTCCACTAATCGTCTCTGAGGTGAACCCTTCCGACAAGGATTCC
                301                                                            360
                R  K  D  D  E  V  P  L  I  V  S  E  V  N  P  S  D  K  D  S

CTGGTCAAGGGCATTATTGCGAATCCTAACTGCACCACCATGGCTGCAATGCCAGTGCTG
                361                                                            420
                L  V  K  G  I  I  A  N  P  N  C  T  T  M  A  A  M  P  V  L

AAGCCACTGCACGATGCCGCTGGTCTTGTAAAGCTTCACGTTTCCTCTTACCAGGCTGTT
                421                                                            480
                K  P  L  H  D  A  A  G  L  V  K  L  H  V  S  S  Y  Q  A  V

TCCGGTTCTGGTCTTGCAGGTGTGGAAACCTTGGCAAAGCAGGTTGCTGCAGTTGGCGAC
                481                                                            540
                S  G  S  G  L  A  G  V  E  T  L  A  K  Q  V  A  A  V  G  D

CACAACGTTGAGTTCGTCCATGATGGACAGGCTGCTGACGCACGGGATGTCGGACCTTAC
                541                                                            600
                H  N  V  E  F  V  H  D  G  Q  A  A  D  A  G  D  V  G  P  Y

GTTTCCCCAATCGCTTACAACGTGCTGGCATTGCCGGAAACCTCGTCGATGACGGCACC
                601                                                            660
                V  S  P  I  A  Y  N  V  L  P  F  A  G  N  L  V  D  D  G  T

TTCGAAACCGACGAAGAGCAGAAGCTGCGCAACGAATCCCGCAAGATTGTCGGCCTCCCA
                661                                                            720
                F  E  T  D  E  E  Q  K  L  R  N  E  S  R  K  I  L  G  L  P

GACCTCAAGGTCTCACGGCACCTGCGTCCGCCTGCCGGTTTTCACCGGCCACACGCTGACC
                721                                                            780
                D  L  K  V  S  G  T  C  V  R  V  P  V  F  T  G  H  T  L  T

ATTCACGCCGAATTCGACAAGGCAATCAGCGTCGAGCAGGCGCAGGAGATCTTGGGTGCC
                781                                                            840
                I  H  A  E  F  D  K  A  I  S  V  E  Q  A  Q  E  I  L  G  A

GCTTCAGGCGTCGAGCTTGTCGACGTCCCAACCCCACTTGGACCTGCCGGCATTGACGAA
                841                                                            900
                A  S  G  V  E  L  V  D  V  P  T  P  L  A  A  A  G  I  D  E

FIG.3A

```
SEQ ID NO: 3     TCCCTCGTTGGACGCATCCGTCAGGACTCCACTGTCGACGACAACCGCGGTCTGGTTCTC
  (CONT.)   901  ------------+------------+------------+------------+------------+  960
SEQ ID NO: 4     S  L  V  G  R  I  R  Q  D  S  T  V  D  D  N  R  G  L  V  L
  (CONT.)

GTCGTATCTGGCGATAACCTTCGCAAGGGCGCAGCACTGAACACCATTCAGATTGCTGAG
           961   ------------+------------+------------+------------+------------+  1020
                 V  V  S  G  D  N  L  R  K  G  A  A  L  N  T  I  Q  I  A  E

CTGCTGGTTAAGTAA
           1021  ---------+-----  1035
                 L  L  V  K  *
```

FIG.3B

Amino Acid sequence of dapB

SEQ ID NO: 5
```
      1 ATGGGAATCAAGGTTGGCGTTCTCGGAGCCAAAGGCCGTGTTGGTCAAACTATTGTGGCA 60
SEQ ID NO: 6
        M  G  I  K  V  G  V  L  G  A  K  G  R  V  G  Q  T  I  V  A

61 GCAGTCAATGAGTCCGACGATCTGGAGCTTGTTGCAGAGATCGGCGTCGACGATGATTTG 120
        A  V  N  E  S  D  D  L  E  L  V  A  E  I  G  V  D  D  L

121 AGCCTTCTGGTAGACAACGGCGCTGAAGTTGTCGTTGACTTCACCACTCCTAACGCTGTG 180
        S  L  L  V  D  N  G  A  E  V  V  V  D  F  T  T  P  N  A  V

181 ATGGGCAACCTGGAGTTCTGCATCAACAACGGCATTTCTGCGGTTGTTGGAACCACGGGC 240
        M  G  N  L  E  F  C  I  N  N  G  I  S  A  V  V  G  T  T  G

241 TTCGATaATGCTCGTCTTGGAGCAGGTTCGGCCTGGCTTGAAGGAAAAGACAATGTCGGT 300
        F  D  N  A  R  L  E  Q  V  R  A  W  L  E  G  K  D  N  V  G

301 GTTCTGATCGCACCTAACTTTGCTATCTCTGCGGTGTTGACCATGGTCTTTTCCAAGCAG 360
        V  L  I  A  P  N  F  A  I  S  A  V  L  T  M  V  F  S  K  Q

361 GCTGCCCGCTTCTTCGAATCAGCTGAAGTTATTGAGCTGCACCACCCAACAAGCTGGAT 420
        A  A  R  F  F  E  S  A  E  V  I  E  L  H  H  P  N  K  L  D

421 GCACCTTCAGGCACCGCGATCCACACTGCTCAGGGCATTGCTGCGGCACGCAAAGAAGCA 480
        A  P  S  G  T  A  I  H  T  A  Q  G  I  A  A  A  R  K  E  A

481 GGCATGGACGCACAGCCAGATGCGACCGAGCAGGCACTTGAGGGTTCCCGTGGCGCAAGC 540
        G  M  D  A  Q  P  D  A  T  E  Q  A  L  E  G  S  R  G  A  S

541 GTAGATGGAATCCCaGTTCAcGCAGTCCGCATGTCCGGCATGCTTGCTCACGAGCAAGTT 600
        V  D  G  I  P  V  H  A  V  R  M  S  G  N  V  A  H  E  Q  V

601 ATCTTTGGCACCCAGGGTCAGACCTTGACCATCAAGCAGGACTCCTATGATCGCAACTCA 660
        I  F  G  T  Q  G  Q  T  L  T  I  K  Q  D  S  Y  D  R  N  S

661 TTTGCACCAGGTGTCTTGGTGGGTGTGCGCAACATTGCACAGCACCCAGGCCTAGTCGTA 720
        F  A  P  G  V  L  V  G  V  R  N  I  A  Q  H  P  G  L  V  V

721 GGACTTGAGCATTACCTAGGCCTGTAA 747
        G  L  E  H  Y  L  G  L  *
```

FIG.4

SEQ ID NO: 10 Amino Acid sequence of ddh

SEQ ID NO: 7
SEQ ID NO: 8

```
        ATGGATTTCGGTAAGCTCGACCAGCACAGTGCCACCACAATTTTCCACCATTACAAGAAC
      1 ....+....+....+....+....+....+....+....+....+....+....+....+  60
        M  H  F  G  K  L  D  Q  D  S  A  T  T  I  L  E  D  Y  K  N

ATGACCAACATCCGCCTAGCTATCGTAGGGTACGGAAACCTGCGACCCAGCGTCGAAAAG
     61 ....+....+....+....+....+....+....+....+....+....+....+....+ 120
        M  T  N  I  R  V  A  I  V  G  Y  G  N  L  G  R  S  V  E  K

CTTATTGCCAAGCAGCCCGACATGGACCTTGTAGGAATCTTCTCGCGCCGGGCCACCCTC
    121 ....+....+....+....+....+....+....+....+....+....+....+....+ 180
        L  I  A  K  Q  P  D  M  D  L  V  G  I  F  S  R  R  A  T  L

GACACAAAGACGCCAGTCTTTGATGTCGCCGACGTGGACAAGCACGCCGACGACGTGGAC
    181 ....+....+....+....+....+....+....+....+....+....+....+....+ 240
        D  T  K  T  P  V  F  D  V  A  D  V  D  K  H  A  D  D  V  D

GTGCTGTTCCTGTGCATGGGCTCCGCCACCGACATCCCTGAGCAGGCACCAAAGTTCGCC
    241 ....+....+....+....+....+....+....+....+....+....+....+....+ 300
        V  L  F  L  C  M  G  S  A  T  D  I  P  E  Q  A  P  K  F  A

CAGTTCGCCTGCACCGTAGACACCTACCACAACCACCGCGACATCCCACGCCACCGCCAG
    301 ....+....+....+....+....+....+....+....+....+....+....+....+ 360
        Q  F  A  C  T  V  D  T  Y  H  N  H  R  D  I  P  R  H  R  Q

GTCATGAACGAAGCCGCCACCGCAGCCGGCAACGTTGCACTGGTCTGTACCGGCTGGGAT
    361 ....+....+....+....+....+....+....+....+....+....+....+....+ 420
        V  M  N  E  A  A  T  A  A  G  N  V  A  L  V  S  T  G  W  D

CCAGGAATGTTCTCCATCAACCGCGTCTACGCAGCCGCACTCTTAGCCGAGCACCAGCAG
    421 ....+....+....+....+....+....+....+....+....+....+....+....+ 480
        P  G  M  F  S  I  N  R  V  Y  A  A  A  V  L  A  E  H  Q  Q

CACACCTTCTGGGGCCCAGGTTTGTCACAGGGCCACTCCGATCCTTTGCGACGCATCCCT
    481 ....+....+....+....+....+....+....+....+....+....+....+....+ 540
        H  T  F  W  G  P  G  L  S  Q  G  H  S  D  P  L  R  R  I  P

GGCGTTCAAAAGGCCGTCCAGTACACCCTGCCATCCGAAGAaGCCCTGCAAAAGGCCCGC
    541 ....+....+....+....+....+....+....+....+....+....+....+....+ 600
        G  V  Q  K  A  V  Q  Y  T  L  P  S  E  E  A  L  E  K  A  R

CGTCGCGAAGCCGGCGACCTcACCGGAAAGCAAACCCAGAAGCGCCAATGCTTCGTGGTT
    601 ....+....+....+....+....+....+....+....+....+....+....+....+ 660
        R  G  E  A  G  D  L  T  G  K  Q  T  H  K  R  Q  C  F  V  V

CCCGATGCGGCCGACCACGAGCGCATCGAAAACGACATCCGCACCATCCCTGATTACTTC
    661 ....+....+....+....+....+....+....+....+....+....+....+....+ 720
        A  D  A  A  D  H  E  R  I  E  N  D  I  R  T  I  P  D  Y  F

GTTGGCTACGAAGTCGAAGTCAACTTCATCGACGAAGCAAGCTTgGACGCCCAGCACACC
    721 ....+....+....+....+....+....+....+....+....+....+....+....+ 780
        V  G  Y  E  V  E  V  N  F  I  D  E  A  T  L  D  A  E  H  T

GGGATGCCACACGGcGGACACGTGATcACCACCGGCGACACCGGTGGCTTCAACCACACC
    781 ....+....+....+....+....+....+....+....+....+....+....+....+ 840
        G  M  P  H  G  G  H  V  I  T  T  G  D  T  G  G  F  N  H  T

GTGGAATACATCCTgAAGCTGGACCGAAACCCAGATTTCACCGCTTCtTCACAGATCCCT
    841 ....+....+....+....+....+....+....+....+....+....+....+....+ 900
        V  E  Y  I  L  K  L  D  R  N  P  D  F  T  A  S  S  Q  I  A

TTCGGccGccCACCTCACCCCATGAAGCAGCAGGGCCAAAGCGGtGCtTTCACCGTGCTC
```

SEQ ID NO: 7     GAAGTTGCTCCATACtTGCTCTCCCCgGAGAACTTGGAtGATCTGATCGCACGCGACGTC
  (CONT.)    961 ------+---------+---------+---------+---------+---------+ 1020
SEQ ID NO: 8     E  V  A  P  Y  L  L  S  P  E  N  L  D  D  L  I  A  R  D  V
  (CONT.)

TAA
    1021 --- 1023
```

FIG.5B

ORF2 Amino Acid sequence

```
SEQ ID NO: 9    GTGGCCGAACAAGTTAAATTGAGCGTGGAGTTGATAGCGTGCAGTTCTTTTACTCCACCC
                1   ....+....|....+....|....+....|....+....|....+....|....+....|   60
SEQ ID NO: 10   M  A  E  Q  V  K  L  S  V  E  L  I  A  C  S  S  F  T  P  P

GCTGATGTTGAGTGGTCAACTCATGTTGAGGGCGCGGAAGCACTCGTCGAGTTTGCGGGT
             61 ....+....|....+....|....+....|....+....|....+....|....+....|  120
                A  D  V  E  W  S  T  D  V  E  G  A  E  A  L  V  E  F  A  G

CGTGCCTGCTACGAAACTTTTGATAAGCCGAACCCTCGAACTGCTTCCAATGCTGCGTAT
            121 ....+....|....+....|....+....|....+....|....+....|....+....|  180
                R  A  C  Y  E  T  F  D  K  P  N  P  R  T  A  S  N  A  A  Y

CTGCGCCACATCATGGAAGTGGGGCACACTGCTTTGCTTGAGCATGCCAATGCCACGATG
            181 ....+....|....+....|....+....|....+....|....+....|....+....|  240
                L  R  H  I  M  E  V  G  H  T  A  L  L  E  H  A  N  A  T  M

TATATCCGAGGCATTTCTCGGTCCGCGACCCATGAATTGGTCCGACACCGCCATTTTTCC
            241 ....+....|....+....|....+....|....+....|....+....|....+....|  300
                Y  I  R  G  I  S  R  S  A  T  H  E  L  V  R  H  R  H  F  S

TTCTCTCAACTGTCTCAGCGTTTCGTGCACAGCGGAGAATCGGAAGTAGTGGTGCCCACT
            301 ....+....|....+....|....+....|....+....|....+....|....+....|  360
                F  S  Q  L  S  Q  R  F  V  H  S  G  E  S  E  V  V  V  P  T

CTCATCGATGAAGATCCGCAGTTGCGTGAACTTTTCATGCACGCCATGGATGAGTCTCGG
            361 ....+....|....+....|....+....|....+....|....+....|....+....|  420
                L  I  D  E  D  P  Q  L  R  E  L  F  M  H  A  M  D  E  S  R

TTCGCTTTCAATGAGCTGCTTAATGCGCTGGAAGAAAAACTTGGCGATGAACCGAATGCA
            421 ....+....|....+....|....+....|....+....|....+....|....+....|  480
                F  A  F  N  E  L  L  N  A  L  E  E  K  L  G  D  E  P  N  A

CTTTTAAGGAAAAAGCAGGCTCGTCAAGCAGCTCGCGCTGTGCTGCCCAACGCTACAGAG
            481 ....+....|....+....|....+....|....+....|....+....|....+....|  540
                L  L  R  K  K  Q  A  R  Q  A  A  R  A  V  L  P  N  A  T  E

TCCAGAATCGTGGTGTCTGGAAACTTCCGACCCTGGAGGCATTTCATTGGCATGCGAGCC
            541 ....+....|....+....|....+....|....+....|....+....|....+....|  600
                S  R  I  V  V  S  G  N  F  R  P  W  R  H  F  I  G  M  R  A

AGTGAACATGCAGACGTCGAAATCCGCGAAGTAGCGGTAGGATGTTTAAGAAAGCTGCAG
            601 ....+....|....+....|....+....|....+....|....+....|....+....|  660
                S  E  H  A  D  V  E  I  R  E  V  A  V  G  C  L  R  K  L  Q

GTAGCAGCGCCAACTGTTTTCGGTGATTTTGAGATTGAAACTTTGGCAGACGGATCGCAA
            661 ....+....|....+....|....+....|....+....|....+....|....+....|  720
                V  A  A  P  T  V  F  G  D  F  E  I  E  T  L  A  D  G  S  Q

ATGGCAACAAGCCCGTATGTCATGGACTTTTAA
            721 ....+....|....+....|....+....|   753
                M  A  T  S  P  Y  V  M  D  F  *
```

FIG. 6

Full length Amino Acid sequence of Lys A (pRS6)

SEQ ID NO: 11    ATGGCTACAGTTGAAAATTTCAATGAACTTCCCGCACACGTATGGCCACGCAATGCCGTG
                 1 ----+----+----+----+----+----+----+----+----+----+----+----+ 60
SEQ ID NO: 12    M  A  T  V  E  N  F  N  E  L  P  A  H  V  W  P  R  N  A  V

CGCCAAGAAGACGGCGTTGTCACCGTCGCTGGTGTGCCTCTGCCTGACCTCGCTGAAGAA
                 61 ----+----+----+----+----+----+----+----+----+----+----+----+ 120
                 R  Q  E  D  G  V  V  T  V  A  G  V  P  L  P  D  L  A  E  E

TACGGAACCCCACTGTTCGTAGTCGACGAGGACGATTTCCGTTCCCGCTGTCGCGACATG
                 121 ----+----+----+----+----+----+----+----+----+----+----+----+ 180
                 Y  G  T  P  L  F  V  V  D  E  D  D  F  R  S  R  C  R  D  M

GCTACCGCATTCGGTGGACCAGGCAATGTGCACTACGCATCTAAAGCGTTCCTGACCAAG
                 181 ----+----+----+----+----+----+----+----+----+----+----+----+ 240
                 A  T  A  F  G  G  P  G  N  V  H  Y  A  S  K  A  F  L  T  K

ACCATTGCACGTTGGGTTGATGAAGAGGGGCTGGCACTGGACATTGCATCCATCAACGAA
                 241 ----+----+----+----+----+----+----+----+----+----+----+----+ 300
                 T  I  A  R  W  V  D  E  E  G  L  A  L  D  I  A  S  I  N  E

CTGGGCATTGCCCTGGCCGCTGGTTTCCCGGCCAGCCGTATCACCGCGCACGGCAACAAC
                 301 ----+----+----+----+----+----+----+----+----+----+----+----+ 360
                 L  G  I  A  L  A  A  G  F  P  A  S  R  I  T  A  H  G  N  N

AAAGGCGTAGAGTTCCTGCGCGCGTTGGTTCAAAACGGTGTGGGACACGTGGTGCTGGAC
                 361 ----+----+----+----+----+----+----+----+----+----+----+----+ 420
                 K  G  V  E  F  L  R  A  L  V  Q  N  G  V  G  H  V  V  L  D

TCCGCACAGGAACTAGAACTGTTGGATTACGTTGCCGCTGGTGAAGGCAAGATTCAGGAC
                 421 ----+----+----+----+----+----+----+----+----+----+----+----+ 480
                 S  A  Q  E  L  E  L  L  D  Y  V  A  A  G  E  G  K  I  Q  D

GTGTTGATCCGCGTAAAGCCAGGCATCGAAGCACACACCGACGAGTTCATCGCCACTAGC
                 481 ----+----+----+----+----+----+----+----+----+----+----+----+ 540
                 V  L  I  R  V  K  P  G  I  E  A  H  T  E  F  I  A  T  S

CACGAAGACCAGAAGTTCGGATTCTCCCTGGCATCCGGTTCCGCATTCGAAGCAGCAAAA
                 541 ----+----+----+----+----+----+----+----+----+----+----+----+ 600
                 H  E  D  Q  K  F  G  F  S  L  A  S  G  S  A  F  E  A  A  K

GCCGCCAACAACGCAGAAAACCTGAACCTGGTTGGCCTGCACTGCCACGTTGGTTCCCAG
                 601 ----+----+----+----+----+----+----+----+----+----+----+----+ 660
                 A  A  N  N  A  E  N  L  N  L  V  G  L  H  C  H  V  G  S  Q

FIG.7A

Lys A (pRS6)

```
SEQ ID NO: 11     GTGTTCGACGCCGAAGGCTTCAAGCTGGCAGCAGAACGCGTGTTGGGCCTGTACTCACAG
  (CONT.)   661   ............+............+............+............+............+............+   720
SEQ ID NO: 12      V  F  D  A  E  G  F  K  L  A  A  E  R  V  L  G  L  Y  S  Q
  (CONT.)

ATCCACAGCGAACTGGGCGTTGCCCTTCCTGAACTGGATCTCGGTGGCGGATACGGCATT
            721   ............+............+............+............+............+............+   780
                   I  H  S  E  L  G  V  A  L  P  E  L  D  L  G  G  G  Y  G  I

GCCTATACCGCAGCTGAAGAACCACTCAACGTCGCAGAAGTTGCCTCCGACCTGCTCACC
            781   ............+............+............+............+............+............+   840
                   A  Y  T  A  A  E  E  P  L  N  V  A  E  V  A  S  D  L  L  T

GCAGTCGGAAAAATGGCAGCGGAACTAGGCATCGACGCACCAACCGTGCTTGTTGAGCCC
            841   ............+............+............+............+............+............+   900
                   A  V  G  K  M  A  A  E  L  G  I  D  A  P  T  V  L  V  E  P

GGCCGCGCTATCGCAGGCCCCTCCACCGTGACCATCTACGAAGTCGGCACCACCAAAGAC
            901   ............+............+............+............+............+............+   960
                   G  R  A  I  A  G  P  S  T  V  T  I  Y  E  V  G  T  T  K  D

GTCCACGTAGACGACGACAAAACCCGCCGTTACATCGCCGTGGACGGAGGCATGTCCGAC
            961   ............+............+............+............+............+............+   1020
                   V  H  V  D  D  D  K  T  R  R  Y  I  A  V  D  G  G  M  S  D

AACATCCGCCCAGCACTCTACGGCTCCGAATACGACGCCCGCGTAGTATCCCGCTTCGCC
           1021   ............+............+............+............+............+............+   1080
                   N  I  R  P  A  L  Y  G  S  E  Y  D  A  R  V  V  S  R  F  A

GAAGGAGACCCAGTAAGCACCCGCATCGTGGGCTCCCACTGCGAATCCGGCGATATCCTG
           1081   ............+............+............+............+............+............+   1140
                   E  G  D  P  V  S  T  R  I  V  G  S  H  C  E  S  G  D  I  L

ATCAACGATGAAATCTACCCATCTGACATCACCAGCGGCGACTTCCTTGCACTCGCAGCC
           1141   ............+............+............+............+............+............+   1200
                   I  N  D  E  I  Y  P  S  D  I  T  S  G  D  F  L  A  L  A  A

ACCGGCGCATACTGCTACGCCATGAGCTCCCGCTACAACGCCTTCACACGGCCCGCCGTC
           1201   ............+............+............+............+............+............+   1260
                   T  G  A  Y  C  Y  A  M  S  S  R  Y  N  A  F  T  R  P  A  V

GTGTCCGTCCGCGCTGGCAGCTCCCGCCTCATGCTGCGCCGCGAAACGCTCGACGACATC
           1261   ............+............+............+............+............+............+   1320
                   V  S  V  R  A  G  S  S  R  L  M  L  R  R  E  T  L  D  D  I
```

FIG.7B

SEQ ID NO: 11    CTCTCACTAGAGGCATAA
   (CONT.) 1321  ----------+--------- 1330
SEQ ID NO: 12    L  S  L  E  A  *

FIG.7C

Truncated ORF2 Amino Acid sequence

```
SEQ ID NO: 13      GTGGCCCAACAAGTTAAATTGAGCGTGCAGTTGATAGCGTGCAGTTCTTTTACTCCACCC
              1    ............+............+............+............+............+............+   60
SEQ ID NO: 14      M  A  E  Q  V  K  L  S  V  E  L  I  A  C  S  S  F  T  P  P

GCTGATGTTGAGTGGTCAACTGATGTTGAGGGCGCGGAAGCACTCGTCGAGTTTGGGGGT
             61    ............+............+............+............+............+............+  120
                   A  D  V  E  W  S  T  D  V  E  G  A  E  A  L  V  E  F  A  G

CGTGCCTGCTACGAAACTTTTGATAAGCCGAACCCTCGAACTGCTTCCAATGCTGCGTAT
            121    ............+............+............+............+............+............+  180
                   R  A  C  Y  E  T  F  D  K  P  N  P  R  T  A  S  N  A  A  Y

CTGCGCCACATCATGGAAGTGGGGCACACTGCTTTGCTTGAGCATGCCAATGCCACGATG
            181    ............+............+............+............+............+............+  240
                   L  R  H  I  M  E  V  G  H  T  A  L  L  E  H  A  N  A  T  M

TATATCCGAGGCATTTCTCGGTCCGCGACCCATGAATTGGTCCGACACCGCCATTTTTCC
            241    ............+............+............+............+............+............+  300
                   Y  I  R  G  I  S  R  S  A  T  H  E  L  V  R  H  R  H  F  S

TTCTCTCAACTGTCTCAGCGTTTCGTGCACAGCGGAGAATCGGAAGTAGTGGTGCCCACT
            301    ............+............+............+............+............+............+  360
                   F  S  Q  L  S  Q  R  F  V  H  S  G  E  S  E  V  V  V  P  T

CTCAT
            361    .....
                   L  (I)
```

FIG.8

Sequence encoded in the HpaI-PvuII fragment containing the P1

SEQ ID NO: 15  AACCGGTGTGGAGCCGACCATTCCGCGAGGCTGCACTGCAACGAGGTCGTAGTTTTGGTACAT
CGCTTCTGGCCAGTTCATGGATTGGCTGCCGAAGAAGCTATAGGCATCGCCACCAGGGCCACC
GGAGTTACCGAAGATGGTGCCGTGCTTTTCGCCTTGGGCAGGGACCTTGACAAAGCCCACGCT
GATATCGCCAAGTGAGGGATCAGAATAGTGCATGGGCACGTCGATGCTGCCACATTGAGCGGA
GGCAATATCTACCTGAGGTGGGCATTCTTCCCAGCGGATGTTTTCTTGCGCTGCTGCAGTGGG
CATTGATACCAAAAAGGGGCTAAGCGCAGTCGAGGCGGCAAGAACTGCTACTACCTTTTTTAT
TGTCGAACGGGGCATTACGGCTCCAAGGACGTTTGTTTTCTGGGTCAGTTACCCCAAAAAGCA
TATACAGAGACCAATGATTTTTCATTAAAAAGGCAGGGATTTGTTATAAGTATGGGTCGTATT
CTGTGCGACGGGTGTACCTCGGCTAGAATTTCTCCCCATGACACCAG

FIG.9

```
            1                                                     50
ATCC 13032                                                    V
N13                                                           C
ATCC 21529                                                    C
  Consensus  MALVVQKYGG SSLESAERIR NVAERIVATK KAGNDVVVVC SAMGDTTDEL 51                                                    100
ATCC 13032
N13
ATCC 21529
  Consensus  LELAAAVNPV PPAREMDMLL TAGERISNAL VAMAIESLGA EAQSFTGSQA 101                                                   150
ATCC 13032
N13
ATCC 21529
  Consensus  GVLTTERHGN ARIVDVTPGR VREALDEGKI CIVAGFQGVN KETRDVTTLG 151                                                   200
ATCC 13032
N13
ATCC 21529
  Consensus  RGGSDTTAVA LAAALNADVC EIYSDVDGVY TADPRIVPNA QKLEKLSFEE 201                                                   250
ATCC 13032
N13
ATCC 21529
  Consensus  MLELAAVGSK ILVLRSVEYA RAFNVPLRVR SSYSNDPGTL IAGSMEDIPV 251                                                   300
ATCC 13032
N13
ATCC 21529
  Consensus  EEAVLTGVAT DKSEAKVTVL GISDKPGEAA KVFRALADAE INIDMVLQNV 301                                                   350
ATCC 13032              S                                    G
N13                     A                                    D
ATCC 21529              A                                    G
  Consensus  SSVEDGTTDI TFTCPRADGR RAMEILKKLQ VQGNWTNLVY DDQVGKVSLV 351                                                   400
ATCC 13032                              T
N13                                     T
ATCC 21529                              I
  Consensus  GAGMKSHPGV TAEFMEALRD VNVNIELIST SEIRISVLIR EDDLDAAARA 401        421
ATCC 13032
N13
ATCC 21529
  Consensus  LHEQFQLGGE DEAVVYAGTG R
```

FIG.10

# POLYNUCLEOTIDE CONSTRUCTS FOR INCREASED LYSINE PRODUCTION

CROSS-REFERENCE TO RELATED APPLICATIONS

This application is a continuation of pending U.S. Utility application Ser. No. 10/067,974, filed on Feb. 8, 2002, the entirety of which is incorporated by reference herein, which claims the right of priority under 35 U.S.C. §119 to U.S. Provisional Appl. No. 60/267,183 filed on Feb. 8, 2001, the entirety of which is also incorporated by reference herein. U.S. Utility application Ser. No. 10/067,974 also claims priority under 35 U.S.G. §120 as a continuation of U.S. Utility application Ser. No. 09/722,441 filed Nov. 28, 2000, now U.S. Pat. No. 6,927,046, which claims priority under 35 U.S.C. §119 (e) to U.S. Provisional Application No. 60/184,130. filed Feb. 22, 2000, and U.S. Provisional Application No. 60/173,707 filed on Dec. 30, 1999.

BACKGROUND OF THE INVENTION

1. Field of the Invention

The invention relates to production of lysine, and provides several isolated polynucleotide molecules useful for the production of L-lysine. One such polynucleotide encodes an aspartate kinase (ask), an aspartate-semialdehyde dehydrogenase (asd) and a dihydrodipicolinate reductase (dapB). Other polypeptides encode ask, asd, dapB and a diaminopimelate dehydrogenase (ddh); ask, asd, dapB, ddh and an ORF2 polypeptide; and ask, asd dapB, ddh, ORF2 and a diaminopimelate decarboxylase (lysA). The invention further provides methods of making and using the polynucleotides, and methods to increase the production of L-lysine.

2. Related Art

L-lysine is an important economic product obtained principally by industrial-scale fermentation utilizing the Gram positive *Corynebacterium glutamicum*, *Brevibacterium flavum* and *Brevibacterium lactofermentum* (Kleemann, A., el. al., Amino Acids, in ULLMANN'S ENCYCLOPEDIA OF INDUSTRIAL CHEMISTRY, vol. A2, pp. 57-97, Weinham: VCH-Verlagsgesellschaft (1985)).

The stereospecificity of the amino acids produced by fermentation makes the process advantageous compared with synthetic processes; generally L-form amino acids are produced by the microbial fermentation process. The production of L-lysine and other amino acids through fermentation, utilizing cheap carbon sources such as molasses, glucose, acetic acid and ethanol, is a relatively inexpensive means of production.

Several fermentation processes utilizing various strains isolated for auxotrophic or resistance properties are known in the art for the production of L-lysine: U.S. Pat. No. 2,979,439 discloses mutants requiring amino acid supplementation (homoserine, or L-methionine and L-threonine); U.S. Pat. No. 3,700,557 discloses mutants having a nutritional requirement for L-threonine, L-methionine, L-arginine, L-histidine, L-leucine, L-isoleucine, L-phenylalanine, L-cystine, or L-cysteine; U.S. Pat. No. 3,707,441 discloses a mutant having a resistance to an L-lysine analog; U.S. Pat. No. 3,687,810 discloses a mutant having both an ability to produce L-lysine and a resistance to bacitracin, penicillin G or polymyxin; U.S. Pat. No. 3,708,395 discloses mutants having a nutritional requirement for homoserine, L-threonine, L-threonine and L-methionine, L-leucine, L-isoleucine or mixtures thereof and a resistance to L-lysine, L-threonine, L-isoleucine or analogs thereof, U.S. Pat. No. 3,825,472 discloses a mutant having a resistance to an L-lysine analog; U.S. Pat. No. 4,169, 763 discloses mutant strains of *Corynebacterium* that produce L-lysine and are resistant to at least one of aspartic analogs and sulfa drugs; U.S. Pat. No. 5,846,790 discloses a mutant strain able to produce L-glutamic acid and L-lysine in the absence of any biotin action-suppressing agent; and U.S. Pat. No. 5,650,304 discloses a strain belonging to the genus *Corynebacterium* or *Brevibacterium* for the production of L-lysine that is resistant to 4-N-(D-alanyl)-2,4-diamino-2,4-dideoxy-L-arabinose 2,4-dideoxy-L-arabinose or a derivative thereof.

A considerable amount is known regarding the biochemical pathway for L-lysine synthesis in *Corynebacterium* species (recently reviewed by Sahm et al., *Ann. N. Y. Acad. Sci.* 782: 25-39 (1996)). Entry into the L-lysine pathway begins with L-aspartate (see FIG. 1), which itself is produced by transamination of oxaloacetate. A special feature of *C. glutamicum* is its ability to convert the L-lysine intermediate piperidine 2,6-dicarboxylate to diaminopimelate by two different routes, i.e. by reactions involving succinylated intermediates or by the single reaction of diaminopimelate dehydrogenase. Overall, carbon flux into the pathway is regulated at two points: first, through feedback inhibition of aspartate kinase by the levels of both L-threonine and L-lysine; and second through the control of the level of dihydrodipicolinate synthase. Therefore, increased production of L-lysine can be obtained in *Corynebacterium* species by deregulating and increasing the activity of these two enzymes.

More recent developments in the area of L-lysine fermentative production involve the use of molecular biology techniques to augment L-lysine production. The following examples are provided: U.S. Pat. Nos. 4,560,654 and 5,236,831 disclose an L-lysine producing mutant strain obtained by transforming a host *Corynebacterium* or *Brevibacterium* species microorganism which is sensitive to S-(2-aminoethyl)-cysteine with a recombinant DNA molecule wherein a DNA fragment conferring both resistance to S-(2-aminoethyl)-cysteine and L-lysine producing ability is inserted into a vector DNA; U.S. Pat. No. 5,766,925 discloses a mutant strain produced by integrating a gene coding for aspartokinase, originating from coryneform bacteria, with desensitized feedback inhibition by L-lysine and L-threonine, into chromosomal DNA of a *Corynebacterium* species bacterium harboring leaky type homoserine dehydrogenase or a *Corynebacterium* species deficient in homoserine dehydrogenase gene; increased L-lysine production is obtained by gene amplification by way of a plasmid vector or utilizing a gene replacement strategy. European Patent Applications EP 0 811 682 A2 and EP 0 854 189 A2 both provide for increased production of L-lysine in *Corynebacterium* species by way of gene amplification based on plasmid copy number.

SUMMARY OF THE INVENTION

It is an object of the invention to provide an isolated polynucleotide molecule, referred herein as the KDB polynucleotide, comprising a nucleic acid molecule encoding an aspartate kinase (ask) polypeptide; a nucleic acid molecule encoding an aspartate-semialdehyde dehydrogenase (asd) polypeptide and a nucleic acid molecule encoding a dihydrodipicolinate reductase (dapB) polypeptide. The polynucleotide may further comprise a nucleic acid encoding a complete or truncated diaminopimelate dehydrogenase (ddh) polypeptide (the KDBH polynucleotide), or a nucleic acid encoding a complete or truncated ORF2 polypeptide (the KDB2 polynucleotide). In addition, the invention provides an isolated polynucleotide molecule, referred herein as the KDB2HL polynucleotide, comprising a nucleic acid molecule encoding an ask, asd, dapB, ddh, ORF2 and diaminopimelate decarboxylase (lysA) polypeptides, in which the ddh, ORF2 and lysA polypeptides may be complete or truncated. In a preferred embodiment, a polynucleotide molecule of the invention further comprises a P1 promoter adjacent to the 5' end of the nucleotide molecule encoding lysA.

It is further the object of the invention to provide a method of increased L-lysine production in a host cell by transforming a host cell with the polynucleotide molecules described above. According to the method of the present invention, the isolated polynucleotide molecules described above are stably integrated into a chromosome of the host cell, or are maintained as extrachromosomal DNA, such as a plasmid, and the transformed host cells are selected for increased L-lysine production.

BRIEF DESCRIPTION OF THE FIGURES

FIG. 2 A, B. The nucleotide (SEQ ID NO:1) and amino acid sequence (SEQ ID NO:2) of ask (ATCC 21529 sequence).

FIG. 3 A, B. The nucleotide (SEQ ID NO:3) and amino acid sequence (SEQ ID NO:4) of asd (ATCC 21529 sequence).

FIG. 4. The nucleotide (SEQ ID NO:5) and amino acid sequence (SEQ ID. NO:6) of dapB (NRRL-B11474).

FIG. 5 A, B. The nucleotide (SEQ ID NO:7) and amino acid sequence (SEQ ID NO:8) of ddh (NRRL-B11474).

FIG. 6. The nucleotide (SEQ ID NO:9) and amino acid sequence (SEQ ID NO: 10) of ORF2.

FIG. 7 A, B, C. The nucleotide (SEQ ID NO: 11) and amino acid sequence (SEQ ID NO: 12) of lysA.

FIG. 8. The nucleotide (SEQ ID NO: 13) and amino acid sequence (SEQ ID NO: 14) of truncated ORF2.

FIG. 9. The nucleotide sequence (SEQ ID NO: 15) of the P1 promoter, the first promoter of the argS-lysA operon from pRS6.

FIG. 10. Comparison of the aspartokinase (ask) amino acid sequence from ATCC13032, N13 and ATCC21529.

DETAILED DESCRIPTION OF THE PREFERRED EMBODIMENTS

A. Definitions

Figure 1:
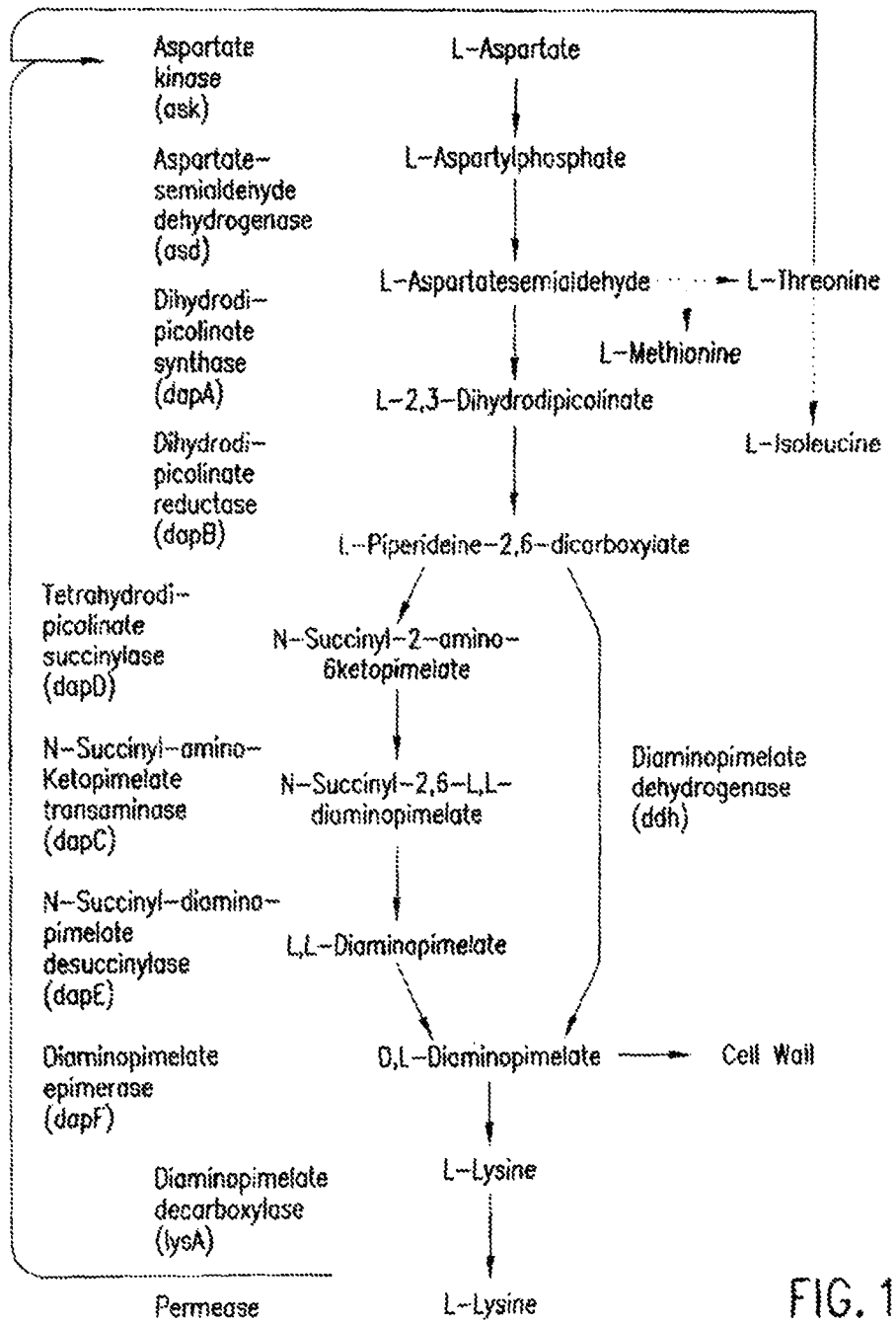
FIG. 1. A schematic of the L-lysine biosynthetic pathway in *Corynebacterium glutamicum*.
Figure 11A:
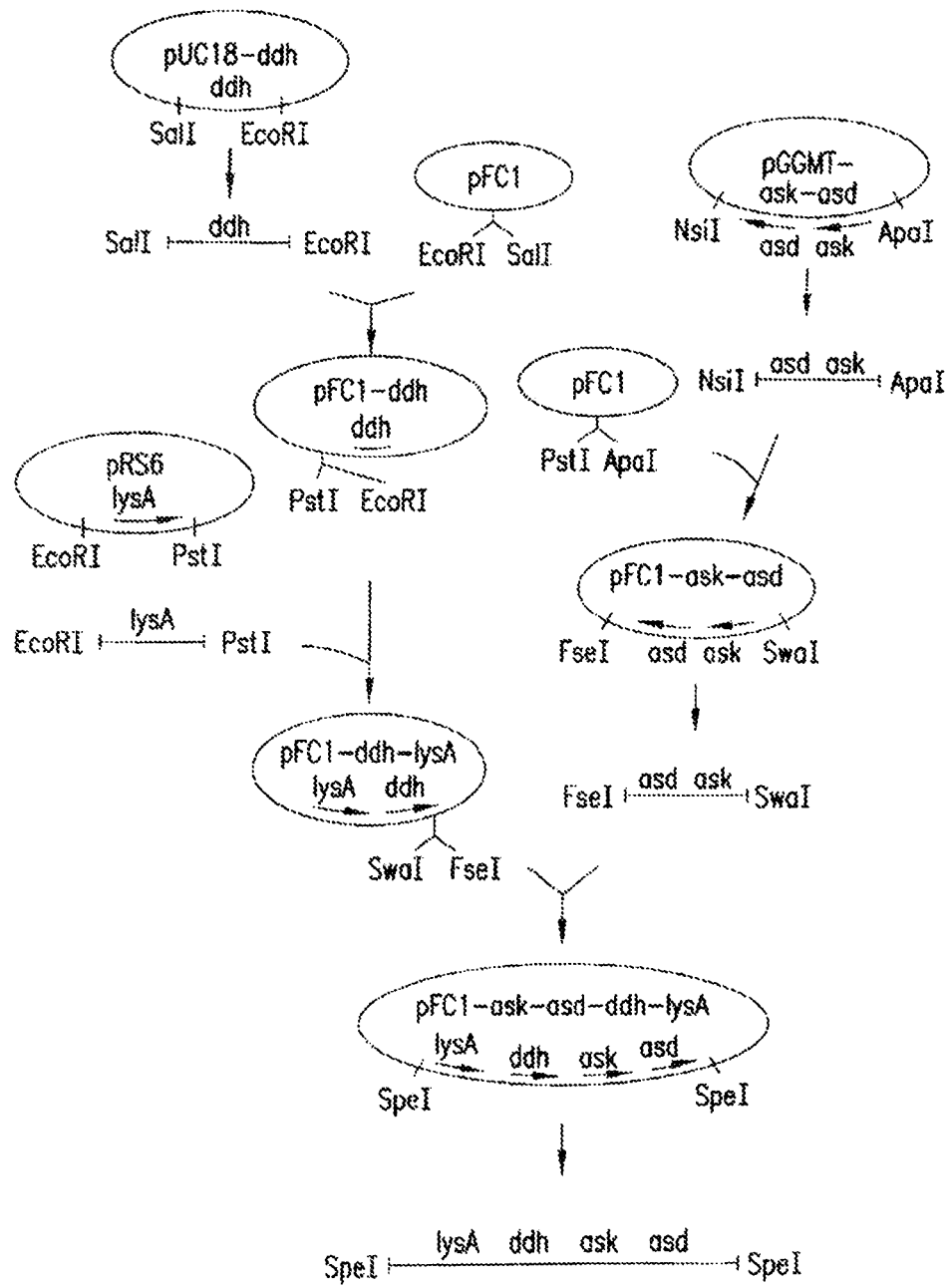
FIGS. 11A and B. A schematic of the construction of the pDElia2$_{FCS}$-KDB construct.
Figure 11B:
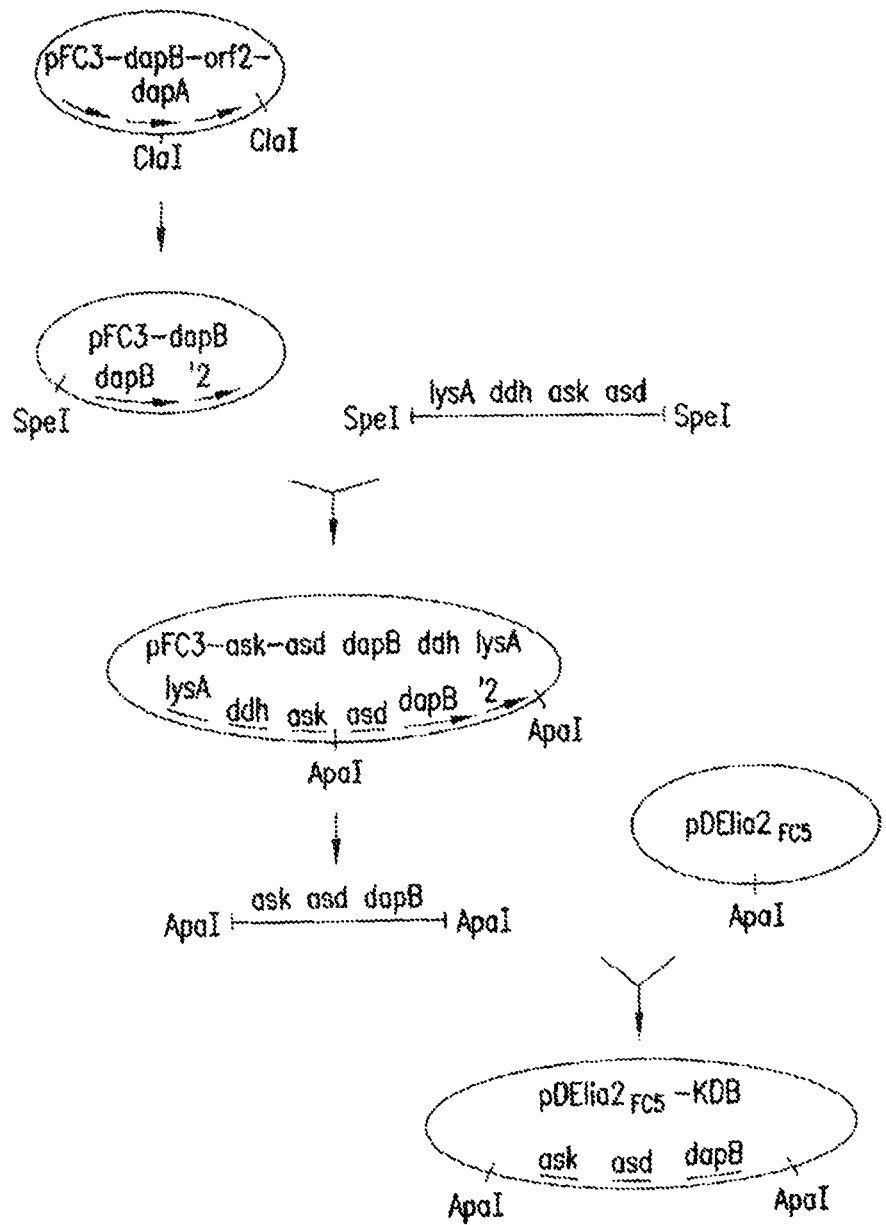
Figure 12:
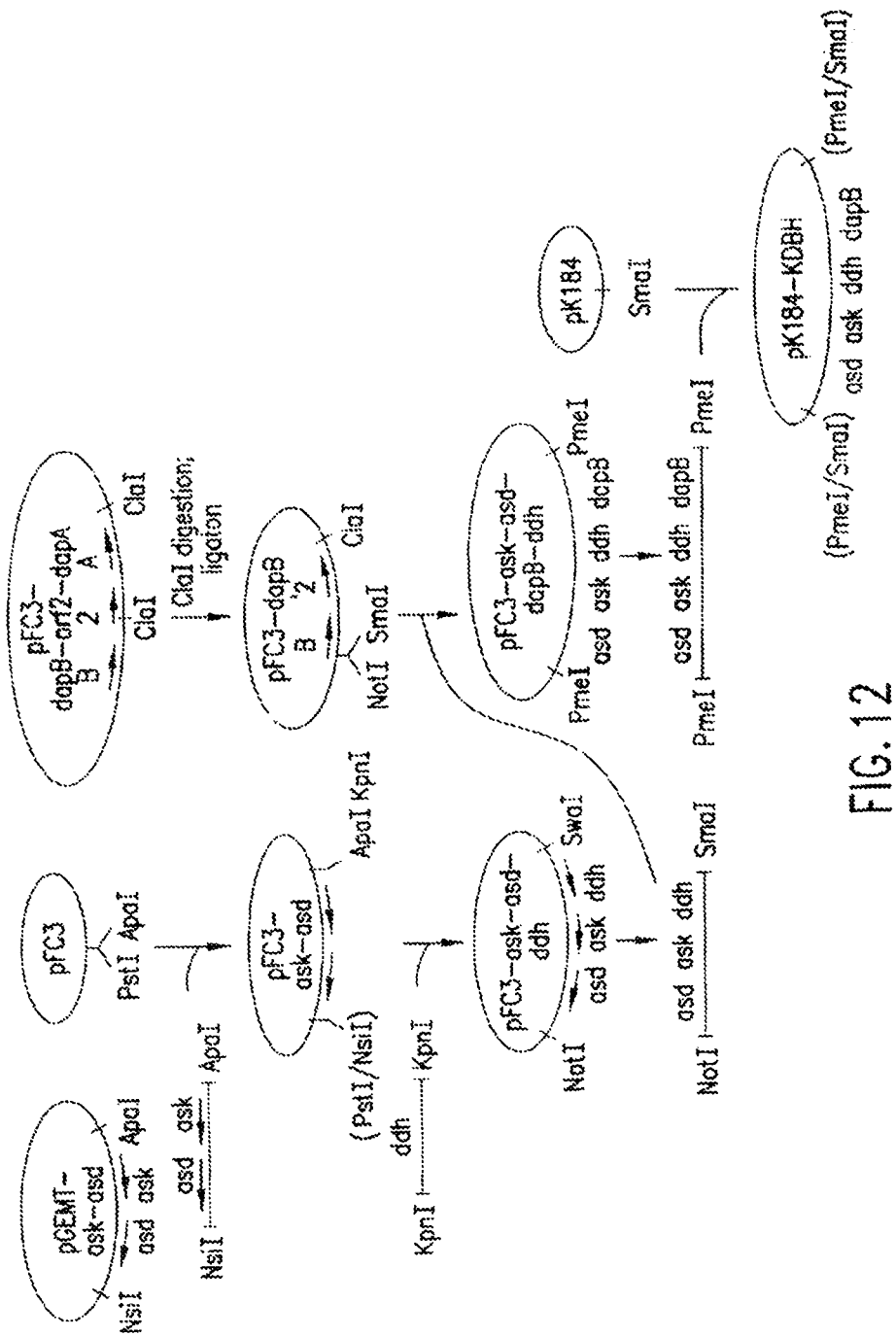
FIG. 12. A schematic of the construction of the pK184-KDBH construct.
Figure 13:
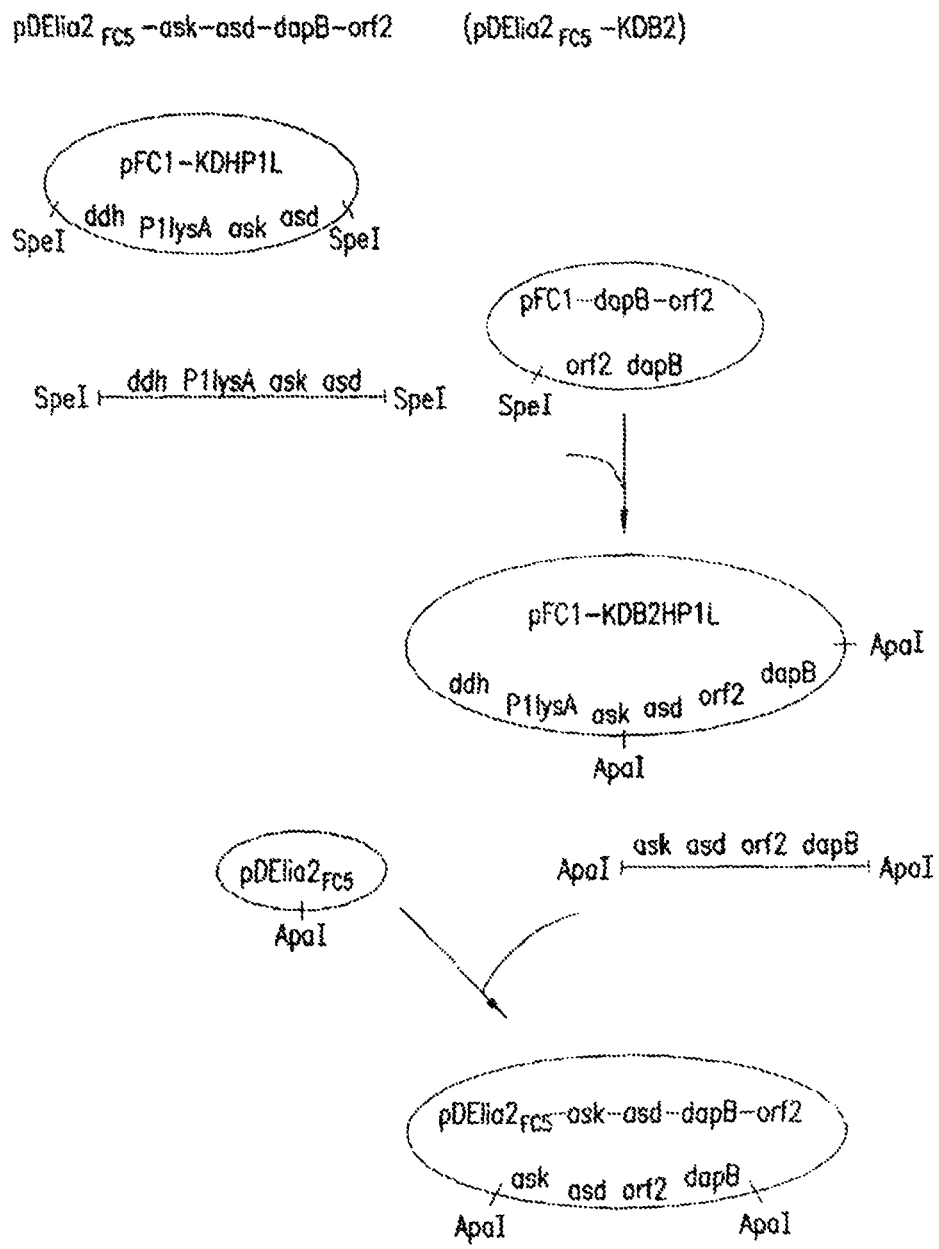
FIG. 13. A schematic of the construction of the pDElia2$_{FCS}$-KDB2 construct.
Figure 14A:
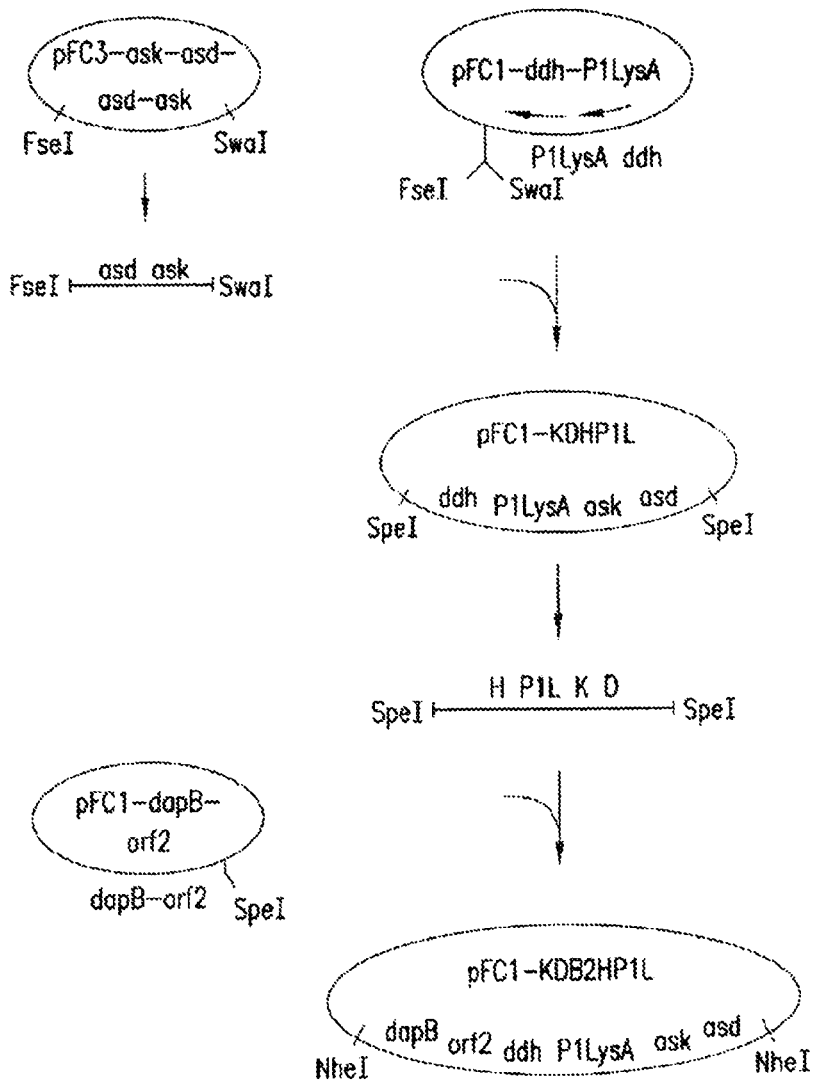
FIG. 14 A, B. A schematic of the construction of the pDElia2$_{FCS}$-KDB2HP1 L construct.
Figure 14B:
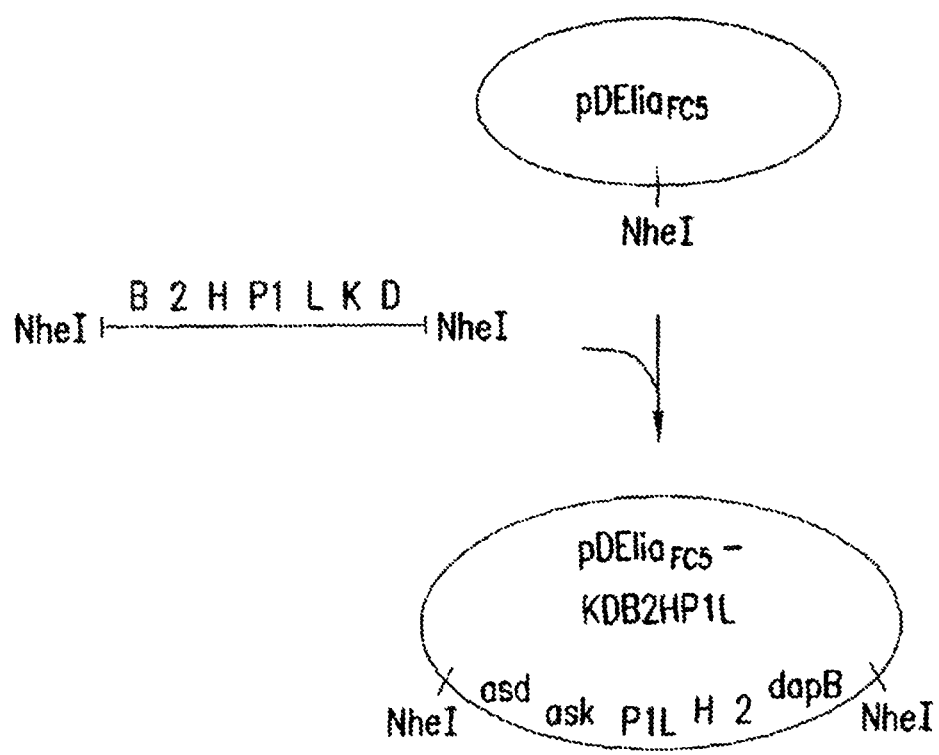

In order to provide a clear and consistent understanding of the specification and claims, including the scope to be given such terms, the following definitions are provided. It is also to be noted that the term "a" or "an" entity, refers to one or more of that entity; for example, "a polynucleotide," is understood to represent one or more polynucleotides.

Auxotroph. As used herein, the term refers to a strain of microorganism requiring for growth an external source of a specific metabolite that cannot be synthesized because of an acquired genetic defect.

Amino Acid Supplement. As used herein, the term refers to an amino acid required for growth and added to minimal media to support auxotroph growth.

Chromosomal Integration. As used herein, the term refers to the insertion of an exogenous DNA fragment into the chromosome of a host organism; more particularly, the term is used to refer to homologous recombination between an exogenous DNA fragment and the appropriate region of the host cell chromosome.

High Yield Derivative. As used herein, the term refers to strain of microorganism that produces a higher yield from dextrose of a specific amino acid when compared with the parental strain from which it is derived.

Host Cell. As used herein, the term "host cell" is intended to be interchangeable with the term "microorganism." Where a difference is intended, the difference will be made clear.

Isolated Nucleic Acid Molecule. As used herein, the term is intended to mean a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Lysine Biosynthetic Pathway Genes. As used herein, the term "lysine biosynthetic pathway gene(s)" is meant to include those genes and genes fragments encoding peptides, polypeptides, proteins, and enzymes, which are directly involved in the synthesis of lysine. These genes can be identical to those which naturally occur within a host cell and are involved in the synthesis of lysine within that host cell. Alternatively, there can be modifications or mutations of such genes, for example, the genes can contain modifications or mutations which do not significantly affect the biological activity of the encoded protein. For example, the natural gene can be modified by mutagenesis or by introducing or substituting one or more nucleotides or by removing nonessential regions of the gene. Such modifications are readily performed by standard techniques.

Lysine Biosynthetic Pathway Protein. As used herein, the term "lysine biosynthetic pathway protein" is meant to include those peptides, polypeptides, proteins, and enzymes, which are directly involved in the synthesis of lysine from aspartate. Also included are amino acid sequences as encoded by open reading frames (ORF), where the ORF is associated with a lysine biosynthetic pathway operon. These proteins can be identical to those which naturally occur within a host cell and are involved in the synthesis of lysine within that host cell. Alternatively, there can be modifications or mutations of such proteins, for example, the proteins can contain modifications or mutations which do not significantly affect the biological activity of the protein. For example, the natural protein can be modified by mutagenesis or by introducing or substituting one or more amino acids, preferably by conservative amino acid substitution, or by removing nonessential regions of the protein. Such modifications are readily performed by standard techniques. Alternatively, lysine biosynthetic proteins can be heterologous to the particular host cell. Such proteins can be from any organism having genes encoding proteins having the same, or similar, biosynthetic roles.

Mutagenesis. As used herein, the term refers to a process whereby a mutation is generated in DNA. With "random" mutagenesis, the exact site of mutation is not predictable, occurring anywhere in the genome of the microorganism, and the mutation is brought about as a result of physical damage caused by agents such as radiation or chemical treatment. rDNA mutagenesis is directed to a cloned DNA of interest, and it can be random or site-directed.

Mutation. As used herein, the term refers to a one or more base pair change, insertion or deletion, or a combination thereof, in the nucleotide sequence of interest.

Operably Linked. As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary, join two protein coding regions, contiguous and in reading frame. However, since enhancers generally function when separated from the promoter by several kilobases and intronic sequences can be of variable lengths, some polynucleotide elements can be operably linked but not contiguous.

Operon. As used herein, the term refers to a contiguous portion of a transcriptional complex in which two or more open reading frames encoding polypeptides are transcribed as a multi-cistronic messenger RNA, controlled by a cis-acting promoter and other cis-acting sequences necessary for efficient transcription, as well as additional cis acting sequences important for efficient transcription and translation (e.g., mRNA stability controlling regions and transcription termination regions). The term generally also refers to a unit of gene expression and regulation, including the structural genes and regulatory elements in DNA.

Parental Strain. As used herein, the term refers to a strain of host cell subjected to some form of treatment to yield the host cell of the invention.

Percent Yield From Dextrose. As used herein, the term refers to the yield of amino acid from dextrose defined by the formula [(g amino acid produced/g dextrose consumed)* 100]=% Yield.

Phenotype. As used herein, the term refers to observable physical characteristics dependent upon the genetic constitution of a host cell.

Promoter. As used herein, the term "promoter" has its art-recognized meaning, denoting a portion of a gene containing DNA sequences that provide for the binding of RNA polymerase and initiation of transcription and thus refers to a DNA sequence capable of controlling the expression of a coding sequence or functional RNA. Promoter sequences are commonly, but not always, found in the 5' non-coding regions of genes. In general, a coding sequence is located 3' to a promoter sequence. Sequence elements within promoters that function in the initiation of transcription are often characterized by consensus nucleotide sequences. The promoter sequence consists of proximal and more distal upstream elements (enhancers). As used herein, the term "endogenous promoter" refers to a promoter sequence which is a naturally occurring promoter sequence in that host microorganism. The term "heterologous promoter" refers to a promoter sequence which is a non-naturally occurring promoter sequence in that host microorganism. The heterologous occurring promoter sequence can be from any prokaryotic or eukaryotic organism. A synthetic promoter is a nucleotide sequence, having promoter activity, and not found naturally occurring in nature.

Promoters can be derived in their entirety from a native gene, or be hybrid promoters. Hybrid promoters are composed of different elements derived from different promoters found in nature, or even comprise synthetic DNA segments. Hybrid promoters can be constitutive, inducible or environmentally responsive.

Useful promoters include constitutive and inducible promoters. Many such promoter sequences are known in the art. See, for example, U.S. Pat. Nos. 4,980,285; 5,631,150; 5,707, 828; 5,759,828; 5,888,783; 5,919,670, and, Sambrook, et al., *Molecular Cloning: A Laboratory Manual,* 2nd Ed., Cold Spring Harbor Press (1989). Other useful promoters include promoters which are neither constitutive nor responsive to a specific (or known) inducer molecule. Such promoters can include those that respond to developmental cues (such as growth phase of the culture), or environmental cues (such as pH, osmoticum, heat, or cell density, for example).

Examples of environmental conditions that can affect transcription by inducible promoters include anaerobic conditions, elevated temperature, or the presence of light. It is understood by those skilled in the art that different promoters can direct the expression of a gene in different cell types, or in response to different environmental conditions. Promoters which cause a gene to be expressed in most cell types at most times are commonly referred to as "constitutive promoters." It is further recognized that since in most cases the exact boundaries of regulatory sequences have not been completely defined, DNA fragments of different lengths can have identical or similar promoter activity.

Relative Growth. As used herein, the term refers to a measurement providing an assessment of growth by directly comparing growth of a parental strain with that of a progeny strain over a defined time period and with a defined medium.

B. Microbiological and Recombinant DNA Methodologies

The present invention relates to a KDB polynucleotide, which comprises a nucleic acid encoding an ask polypeptide, a nucleic acid molecule encoding an asd polypeptide and a nucleic acid molecule encoding a dapB polypeptide, wherein "K" represents a nucleotide sequence encoding the ask polypeptide; "D" represents a nucleotide sequence encoding the asd polypeptide; and "B" represents a nucleotide sequence encoding the dapB polypeptide.

In one embodiment the present invention relates to an isolated KDB polynucleotide molecule comprising:
1. a nucleic acid molecule encoding an aspartate kinase (ask) polypeptide;
2. a nucleic acid molecule encoding an aspartate-semialdehyde dehydrogenase (asd) polypeptide; and
3. a nucleic acid molecule encoding a dihydrodipicolinate reductase (dapB) polypeptide.

In another embodiment, the KDB polynucleotide molecule consists essentially of a nucleic acid molecule encoding an ask polypeptide, a nucleic acid molecule encoding an asd polypeptide and a nucleic acid molecule encoding a dapB polypeptide.

The present invention also relates to a KDBH polynucleotide, which comprises a nucleic acid encoding an ask polypeptide, a nucleic acid molecule encoding an asd polypeptide, a nucleic acid molecule encoding a dapB polypeptide and a nucleic acid molecule encoding a ddh polypeptide, wherein "K" represents a nucleotide sequence encoding the ask polypeptide; "D" represents a nucleotide sequence encoding the asd polypeptide; "B" represents a nucleotide sequence encoding the dapB polypeptide; and "H" represents a nucleotide sequence encoding the ddh polypeptide.

In one embodiment, the KDBH polynucleotide molecule additionally comprises a nucleic acid encoding a complete or truncated ORF2 polypeptide.

The present invention also relates to a KDB2 polynucleotide, which comprises a nucleic acid encoding an ask polypeptide, a nucleic acid molecule encoding an asd polypeptide, a nucleic acid molecule encoding a dapB polypeptide and a nucleic acid molecule encoding an ORF2 polypeptide, and wherein "K" represents a nucleotide sequence encoding the ask polypeptide; "D" represents a nucleotide sequence encoding the asd polypeptide; "B" represents a nucleotide sequence encoding the dapB polypeptide; and "2" represents a nucleotide sequence encoding the ORF2 polypeptide.

The present invention also relates to a KDB2HL polynucleotide, which comprises a nucleotide encoding an ask polypeptide, a nucleic acid molecule encoding an asd polypeptide, a nucleic acid molecule encoding a dapB polypeptide, a nucleic acid molecule encoding an ORF2 polypeptide, a nucleic acid molecule encoding a ddh polypeptide and a nucleic acid molecule encoding a lysA polypeptide. In a preferred embodiment, the KDB2HL polynucleotide molecule also comprises a P1 promoter adjacent to the 5' end of the nucleic acid encoding the lysA polypeptide.

In a preferred embodiment, the polynucleotide molecules of the present invention do not comprise any nucleic acid molecules encoding any lysine pathway polypeptides other than ask, asd, dapB, ddh, ORF2 and lysA.

In one embodiment, an ask polypeptide is defined as a polypeptide having the enzymatic activity of bacterial aspartate kinase. Bacterial aspartate kinase enzymatic activity converts L-aspartate to L-aspartylphosphate. In a preferred embodiment, an ask polypeptide would have the enzymatic activity of aspartate kinase from ATCC21529. In a preferred embodiment, the isolated ask amino sequence disclosed in SEQ ID NO:2 possesses unique properties with respect to feedback resistance of ask enzyme activity to accumulated levels of L-lysine and L-threonine in the culture medium. When compared to the DNA sequences of other *Corynebacterium glutamicum* ask-asd gene sequences, a threonine to isoleucine change at amino acid residue 380 which results in resistance to feedback inhibition is observed. Other amino acid changes at residue 380 can also result in decreased ask enzyme sensitivity to L-threonine and/or L-lysine.

An asd polypeptide is defined as a polypeptide having the enzymatic activity of aspartate-semialdehyde dehydrogenase. Aspartate-semialdehyde dehydrogenase enzymatic activity converts L-aspartylphosphate to L-aspartatesemialdehyde. In a preferred embodiment, an asd polypeptide would have the enzymatic activity of aspartate-semialdehyde dehydrogenase from ATCC21529.

A dapB polypeptide is defined as a polypeptide having the enzymatic activity of dihydrodipicolinate reductase. Dihydrodipicolinate reductase enzymatic activity converts L-2,3-dihydrodipicolinate to L-piperideine-2,6-dicarboxylate. In a preferred embodiment, a dapB polypeptide would have the enzymatic activity of dihydrodipicolinate reductase from NRRL-B11474.

A ddh polypeptide is defined as a polypeptide having the enzymatic activity of diaminopimelate dehydrogenase. Diaminopimelate dehydrogenase enzymatic activity converts L-piperideine-2,6-dicarboxylate to D,L-diaminopimelate. In a preferred embodiment, a ddh polypeptide would have the enzymatic activity of diaminopimelate dehydrogenase from NRRL-B11474.

A lysA polypeptide is defined as a polypeptide having the enzymatic activity of diaminopimelate decarboxylase. Diaminopimelate decarboxylase activity converts D,L-diaminopimelate to L-lysine. In a preferred embodiment, a lysA polypeptide would have the enzymatic activity of diaminopimelate decarboxylase from ASO19.

Ask, asd, dapB, ddh, ORF2 and lysA polypeptides encoded by the polynucleotide molecules of the present invention can be truncated forms of the polypeptides encoded by the genomic copies of the ATCC21529 ask and asd genes, the NRRL-B11474 dapB, ddh, ORF2 genes and the ASO19 lysA gene.

It should be noted that in addition to the indicated polypeptide sequences encoded by the isolated nucleic acid sequences represented by "K", "D", "B", "H," "2" and "L," these isolated nucleic acid sequences can also include native promoter elements for the operons represented therein. Thus, the ask-asd sequences can include the respective native ask-asd operon elements, and the dapB and ddh sequences can include their respective native promoter elements. The preferred promoter for the nucleotide molecule encoding the lysA polypeptide is the P1 promoter, the first promoter from the argS-lysA operon.

The invention as provided herein utilizes some methods and techniques that are known to those skilled in the arts of microbiology and recombinant DNA technologies. Methods and techniques for the growth of bacterial cells, the introduction of isolated DNA molecules into host cells, and the isolation, cloning and sequencing of isolated nucleic acid molecules, etc., are a few examples of such methods and techniques. These methods and techniques are described in many standard laboratory manuals, such as Davis et al., *Basic Methods In Molecular Biology* (1986), J. H. Miller, *Experiments in Molecular Genetics*, Cold Spring Harbor Laboratory Press, Cold Spring Harbor, N.Y. (1972); J. H. Miller, *A Short Course in Bacterial Genetics*, Cold Spring Harbor Laboratory Press, Cold Spring Harbor, N.Y. (1992); M. Singer and P. Berg, *Genes & Genomes*, University Science Books, Mill Valley, Calif. (1991); J. Sambrook, E. F. Fritsch and T. Maniatis, *Molecular Cloning: A Laboratory Manual,* 2d ed., Cold Spring Harbor Laboratory Press, Cold Spring Harbor, N.Y. (1989); P. B. Kaufman et al., *Handbook of Molecular and Cellular Methods in Biology and Medicine*, CRC Press, Boca Raton, Fla. (1995); *Methods in Plant Molecular Biology and Biotechnology*, B. R. Glick and J. E. Thompson, eds., CRC Press, Boca Raton, Fla. (1993); and P. F. Smith-Keary, *Molecular Genetics of Escherichia coli*, The Guilford Press, New York, N.Y. (1989), all of which are incorporated herein by reference in their entireties.

In a preferred embodiment, a nucleic acid molecule encoding an ask polypeptide would be at least 90%, 91%, 92%, 93%, 94%, 95%, 96%, 97%, 98% or 99% identical to SEQ ID NO:1. A nucleic acid molecule encoding an asd polypeptide would be at least 90%, 91%, 92%, 93%, 94%, 95%, 96%, 97%, 98% or 99% identical to SEQ ID NO:3. a nucleic acid molecule encoding a dapB polypeptide would be at least 90%, 91%, 92%, 93%, 94%, 95%, 96%, 97%, 98% or 99% identical to SEQ ID NO:5, a nucleic acid molecule encoding a ddh polypeptide would be at least 90%, 91%, 92%, 93%, 94%, 95%, 96%, 97%, 98% or 99% identical to SEQ ID NO:7, a nucleic acid encoding an ORF2 polypeptide would be at least 90%, 91%, 92%, 93%, 94%, 95%, 96%, 97%, 98%, 99% or 100% identical to SEQ ID NO:9 and a nucleic acid encoding a lysA polypeptide would be at least 90%, 91%, 92%, 93%, 94%, 95%, 96%, 97%, 98%, 99% or 100% identical to SEQ ID NO:11 or the complement thereof. In a preferred embodiment the nucleic acid sequence of a P1 promoter would be at least 90%, 91%, 92%, 93%, 94%, 95%, 96%, 97%, 98%, 99% or 100% identical to SEQ ID NO:15. In one embodiment, a nucleic acid encoding a truncated ORF2 polypeptide would be at least 90%, 91%, 92%, 93%, 94%, 95%, 96%, 97%, 98%, 99% or 100% identical to SEQ ID NO:13.

As one skilled in the art would know, any strain of *Corynebacterium* species, particularly that of *Corynebacterium glutamicum*, can be utilized for the isolation of nucleic acid molecules that will be used to amplify the number of chromosomally located amino acid biosynthetic pathway genes. Particularly preferred strains include: NRRL-B11474, ATCC 21799, ATCC 21529, ATCC 21543, and E12.

As a practical matter, whether any particular nucleic acid sequence is at least 90%, 91%, 92%, 93%, 94%, 95%, 96%, 97%, 98% or 99% identical to, for instance, a nucleotide sequence consisting of SEQ ID NO:1, SEQ ID NO:3; SEQ ID NO:5; SEQ ID NO:7; SEQ ID NO:9; SEQ ID NO:11; SEQ ID NO:13; SEQ ID NO:15, or a complementary sequence thereof, can be determined conventionally using sequence analysis computer programs such as a OMIGA® Version 2.0 for Windows, available from Oxford Molecular, Ltd. (Oxford, U.K.). OMIGA uses the CLUSTAL W alignment algorithm using the slow full dynamic programming alignment method with default parameters of an open gap penalty of 10 and an extend gap penalty of 5.0, to find the best alignment between two nucleotide sequences. When using CLUSTAL W or any other sequence alignment program to determine whether a particular sequence is, for instance, 95% identical to a reference sequence according to the present invention, the parameters are set, of course, such that the percentage of identity is calculated over the full length of the reference nucleotide sequence such that gaps, mismatches, or insertions of up to 5% of the total number of nucleotides in the reference sequence are allowed. Other sequence analysis programs, known in the art, can be used in the practice of the invention.

Unless otherwise indicated, all nucleotide sequences described herein were determined using an automated DNA sequencer (such as the Model 373 from Applied Biosystems, Inc.), and all amino acid sequences of polypeptides encoded by DNA molecules described herein were predicted by translation of the relative DNA sequence. Therefore, as is known in the art, for any DNA sequence determined by this automated approach, any nucleotide sequence determined herein can contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art.

It is known in the art that amino acids are encoded at the nucleic acid level by one or more codons (code degeneracy). It is also known in the art that choice of codons may influence expression of a particular amino acid sequence (protein, polypeptide, etc.). Thus, the invention is further directed to nucleic acid molecules encoding the ask amino acid sequence of SEQ ID NO:2 wherein the nucleic acid molecule comprises any codon known to encode a particular amino acid. Likewise, the invention is directed to KDB, KDBH, KDB2 and KDB2HL polynucleotides comprising nucleic acid sequences which comprise alternative codons in order to optimize expression of the protein or polypeptide.

It will be recognized in the art that some amino acid sequences of the invention can be varied without significant effect of the structure or function of the proteins disclosed herein. Variants included can constitute deletions, insertions, inversions, repeats, and type substitutions so long as enzyme activity is not significantly affected. Guidance concerning which amino acid changes are likely to be phenotypically silent can be found in Bowie, J. U., et al., "Deciphering the Message in Protein Sequences: Tolerance to Amino Acid Substitutions," *Science* 247:1306-1310 (1990).

It is preferred that the polypeptides obtained by the expression of the polynucleotide molecules of the present invention would have at least approximately 80%, 90%, 95%, 96%, 97%, 98%, 99% or 100% identity to one or more amino acid sequences selected from the group comprising SEQ ID No: 2, 4, 6, 8, 10, 12 and 14. A truncated ORF2 polypeptide has at least about 25% of the full length of an ORF2 polypeptide, preferably the ORF2 polypeptide of SEQ ID NO: 10. In one embodiment, a truncated ORF2 polypeptide has the sequence of SEQ ID NO: 14. By a polypeptide having an amino acid sequence at least, for example, 95% "identical" to a reference amino acid sequence of a polypeptide is intended that the amino acid sequence of the claimed polypeptide is identical to the reference sequence except that the claimed polypeptide sequence can include up to five amino acid alterations per each 100 amino acids of the reference amino acid of the polypeptide. In other words, to obtain a polypeptide having an amino acid sequence at least 95% identical to a reference amino acid sequence, up to 5% of the amino acid residues in the reference sequence can be deleted or substituted with another amino acid, or a number of amino acids up to 5% of the total amino acid residues in the reference sequence can be inserted into the reference sequence. These alterations of the reference sequence can occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 92%, 95%, 96%, 97%, 98% or 99% identical to, for instance, the amino acid sequence shown in SEQ ID NO:2, 4, 6, 8, 10, 12, 14 or to the amino acid sequence encoded by a nucleic acid sequence can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference sequence (query sequence, a sequence of the present invention) and a subject sequence, also referred to as a global sequence alignment, is determined using the FASTDB computer program based on the algorithm of Brutlag et al. (Comp. App. Biosci. 6:237-245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity.

For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for.

C. Methods and Processes of the Invention

Various embodiments of the invention provide methods of utilizing the KDB, KDBH, KDB2 and KDB2HL polynucleotide molecules. In a preferred embodiment, any one of these polynucleotide molecules is utilized to increase the production of lysine from a host cell.

The amino acid pathway for L-lysine biosynthesis is well known to skilled artisans of amino acid production. Genes encoding the enzymes important for the conversion of L-aspartate to L-lysine include the ask, asd, dapA, dapB, ddh and lysA genes (FIG. 1). Thus, the invention provides herein specific embodiments utilizing L-lysine biosynthetic pathway genes.

The isolated polynucleotide molecules of the invention are preferably propagated and maintained in an appropriate nucleic acid vector. Methods for the isolation and cloning of the isolated nucleic acid molecules of the invention are well known to those skilled in the art of recombinant DNA technology. Appropriate vectors and methods for use with prokaryotic and eukaryotic hosts are described by Sambrook et al., *Molecular Cloning: A Laboratory Manual*, Second Edition, Cold Spring Harbor, N.Y., 1989, the disclosure of which is hereby incorporated by reference.

A great variety of vectors can be used in the invention. Such vectors include chromosomal, episomal and virus-derived vectors, e.g., vectors derived from bacterial plasmids and from bacteriophage, as well as vectors derived from combinations thereof, such as those derived from plasmid and bacteriophage genetic elements, such as cosmids and phagemids, all can be used in accordance with this aspect of the present invention. Retroviral vectors can be replication competent or replication defective. In the latter case, viral propagation generally will occur only in complementing host cells. Preferred, are vectors suitable to maintain and propagate a polynucleotide in a bacterial host.

A large numbers of suitable vectors and promoters for use in bacteria are known, many of which are commercially available. Preferred prokaryotic vectors include plasmids such as those capable of replication in *E. coli* (such as, for example, pBR322, ColE1, pSC101, pACYC 184, πVX). Such plasmids are, for example, disclosed by Maniatis, T., et al., In. *Molecular Cloning*, A Laboratory Manual, Cold Spring Harbor Press, Cold Spring Harbor, N.Y. (1982)). The following vectors are provided by way of example: pET (Novagen), pQE70, pQE60, pQE-9 (Qiagen), pBs, phagescript, psiX174, pBlueScript SK, pBsKS, pNH8a, pNH16a, pNH18a, pNH46a (Stratagene), pTrc99A, pKK223-3, pKK233-3, pDR540, pRIT5 (Pharmacia).

Preferred vectors for the isolated nucleic acid molecules of the invention include the pFC1 to pFC7 novel family of combinatorial cloning vectors (Lonsdale, D. M., et al., *Plant Molecular Biology Reporter* 13: 343-345 (1995)) and the pK184 vector (Jobling, M. G. and Homes, R. K., *Nucleic Acid Research* 18: 5315-5316 (1990)).

Another group of preferred vectors are those that are capable of autonomous replication in *Corynebacterium* species. Such vectors are well known to those skilled in the art of amino acid production by way of microbial fermentation, examples of which include pSR1, pMF1014α and vectors derived therefrom. Other suitable vectors will be readily apparent to the skilled artisan.

A KDB, KDBH, KDB2 or KDB2HL polynucleotide can be joined to a vector containing a selectable marker for propagation in a host. The vectors can include at least one selectable marker. In this regard, vectors preferably contain one or more selectable marker genes to provide a phenotypic trait for selection of transformed host cells. Such markers include dihydrofolate reductase, G418 or neomycin resistance for eukaryotic cell culture and tetracycline, kanamycin or ampicillin resistance genes, or an autotrophic gene which allows the host cell to grow in the absence of a nutrient for which the host cell strain is normally autotrophic.

Representative examples of appropriate hosts include, but are not limited to, bacterial cells, such as *E. coli*, *Streptomyces* and *Salmonella* typhimurium cells; fungal cells, such as yeast cells and insect cells such as Drosophila S2 and Spodoptera Sf9 cells. Appropriate culture mediums and conditions for the above-described host cells are known in the art.

If the vector is intended to be maintained in the host cell extrachromosomally, it will contain, in addition and origin of replication which will allow it to replicate in the host cell. Alternatively, if it is desired that the vector integrate into the chromosome, the vector is constructed such that it cannot replicate in the host cell. For example, such a vector might be capable of propagation in another organism, for example, *E. coli*, but lack the proper origin of replication to be propagated in *Corynebacterium*. In another aspect of this embodiment, the vector is a shuttle vector which can replicate and be maintained in more than one host cell species, for example, such a shuttle vector might be capable of replication in a *Corynebacterium* host cell such as a *C. glutamicum* host cell, and also in an *E. coli* host cell.

In one embodiment of the invention, the additional copies of the L-lysine biosynthesis pathway gene(s) selected from ask, asd, dapB, ddh, ORF2 and lysA can be integrated into the chromosome. Another embodiment of the invention provides that the additional copies of the L-lysine biosynthesis pathway gene(s) are carried extra-chromosomally. Amplifications by a factor of 5 or less can be obtained by introducing the additional gene copies into the chromosome of the host strain by way of single event homologous recombination. In a most preferred embodiment, the recombination event results in the introduction of one additional copy of the copy of the gene or genes of interest. If more than 5 copies of the genes are desired, multicopy plasmids carrying the recombinant DNA construct of the invention can be utilized.

In another embodiment of the invention, enzyme activity is increased by overexpressing one or more genes of the group comprising ask, asd, dapB, ddh, ORF2 and lysA encoding one or more lysine biosynthetic pathway enzymes. In one embodiment of the invention, said one or more genes are operably linked directly or indirectly to one or more promoter sequences. In another embodiment of the invention, said operably linked promoter sequences are heterologous, endogenous, or hybrid. In a preferred embodiment of the invention, said promoter sequences are one or more of: a promoter sequence from the 5' end of genes endogenous to C. glutamicum, a promoter sequence from plasmids that replicate in C. glutamicum, and, a promoter sequence from the genome of phage which infect C. glutamicum. In another embodiment, one or more of said promoter sequences are modified. In another preferred embodiment, said modification comprises truncation at the 5' end, truncation at the 3' end, non-terminal insertion of one or more nucleotides, non-terminal deletion of one or more nucleotides, addition of one or more nucleotides at the 5' end, addition of one or more nucleotides at the 3' end, and, combinations thereof. In a preferred embodiment, the P1 promoter, the first promoter of the argS-lysA operon is used as the promoter for the lysA gene.

Alternative gene promoter elements can be utilized in the constructs of the invention. For example, known bacterial promoters suitable for this use in the present invention include the E. coli lacI and lacZ promoters, the T3 and T7 promoters, the gpt promoter, the lambda PR and PL promoters, the trp promoter, or promoters endogenous to the bacterial cells of the present invention. Other promoters useful in the invention include regulated promoters, unregulated promoters and heterologous promoters. Many such promoters are known to one of skill in the art. See Sambrook, E. F. et al., *Molecular Cloning: A Laboratory Manual,* 2d ed., Cold Spring Harbor Laboratory Press, Cold Spring Harbor, N.Y. (1989).

In addition, the vector can contain control regions that regulate as well as engender expression. Generally, such regions will operate by controlling transcription, such as inducer or repressor binding sites and enhancers, among others.

In a preferred embodiment of the invention, the KDB polynucleotide molecule is encompassed in vector pDElia2$_{FC5}$-KDB. In another preferred embodiment, the KDBH polynucleotide molecule is encompassed in vector pK184-KDBH. In another preferred embodiment, the KDB2 polynucleotide molecule is encompassed in vector pDElia2$_{FC5}$-KDB2. In a further preferred embodiment, the KDB2HL polynucleotide is encompassed in vector pDElia2$_{FC5}$-KDB2HL.

It is a further object of the invention to provide a host cell comprising a vector comprising any one of the isolated KDB, KDBH, KDB2 or KDB2HL polynucleotide molecule.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). If the vector is a virus, it can be packaged in vitro using an appropriate packaging cell line and then transduced into host cells.

Representative examples of appropriate hosts for the above described isolated nucleic acid molecules include, but are not limited to, bacterial cells, such as *C. glutamicum, Escherichia coli, Streptomyces* and *Salmonella typhimurium* cells; and fungal cells, such as yeast cells. Appropriate culture media and conditions for the above-described host cells are known in the art.

Bacterial cells, such as *E. coli* and coryneform bacteria are preferred as host cells. Particularly preferred *Corynebacterium* and *Brevibacterium* species of the methods and processes of the invention include: *Corynebacterium glutamicum, Brevibacterium flavum, Brevibacterium lactofermentum* and other *Cornynebacteria* and *Brevibacteria* species known in the art.

As will be understood by those skilled in the art, the term "*Corynebacterium* species" includes those organisms previously identified in the literature as "*Brevibacterium* species," for example *Brevibacterium flavum* and *Brevibacterium lactofermentum* which have now been reclassified into the genus *Corynebacterium* (*Int. J. Syst. Bacteriol.* 41: 255 (1981)).

It is a further object to provide a host cell wherein said host cell is a *Brevibacterium* selected from the group consisting of *Brevibacterium flavum* NRRL-B30218, *Brevibacterium flavum* NRRL-B30458, *Brevibacterium flavum* NRRL-B30410, *Brevibacterium flavum* NRRL-B30459, *Brevibacterium flavum* NRRL-B30522, *Brevibacterium flavum* NRRL-B30219, *Brevibacterium lactofermentum* NRRL-B30220, *Brevibacterium lactofermentum* NRRL-B30221, *Brevibacterium lactofermentum* NRRL-B30222, *Brevibacterium flavum* NRRL-30234 and *Brevibacterium lactofermentum* NRRL-30235. In another embodiment, the host cell is *Escherichia coli*. In a preferred embodiment, the host cell is *E. coli* DH5 α MCR NRRL-B30228. In another embodiment, the host cell is a *C. glutamicum* selected from the group consisting of *C. glutamicum* NRRL-B30236 and *C. glutamicum* NRRL-B30237.

The methods to increase the production of lysine and the processes for the production of lysine of the invention can both utilize a step requiring the transformation of an isolated nucleic acid molecule into a host cell.

The methods to increase the production of lysine and the processes for the production of lysine of the invention can utilize a step requiring amplification of at least one lysine biosynthesis pathway gene. As known to one skilled in the art, the term amplification means increasing the number of a gene or genes of lysine biosynthetic pathway by any means known in the art. Particularly preferred means of amplification include: (1) the addition an isolated KDB, KDBH, KDB2 or KDB2HL polynucleic acid molecule by insertion into the chromosome of a host cell, for example by homologous recombination, and (2) the addition an isolated KDB, KDBH, KDB2 or KDB2HL polynucleic acid molecule into a host cell by way of a self-replicating, extra-chromosomal vector, for example, a plasmid.

Methods of inserting an isolated nucleic acid molecule into the chromosome of a host cell are known to those skilled in the art. For example, insertion of isolated nucleic acid molecules into the chromosome of *Corynebacterium* species can be done utilizing the pK184 plasmid described by Jobling, M. et al., *Nucleic Acids Research* 18(17): 5315-5316 (submitted 1990). Because these vectors lack a *Corynebacterium* species origin of replication and contain a selectable marker such as kanamycin (kan), cells will only be capable of growing under selection if the vector has been inserted into the host cell chromosome by homologous recombination.

In alternative embodiments, the invention also provides methods for increasing lysine production and processes for the production of lysine wherein biosynthetic pathway gene amplification is accomplished through the introduction into a host cell of a self-replicating, extra-chromosomal vector, e.g., a plasmid, comprising an isolated KDB, KDBH, KDB2 or KDB2HL polynucleotide molecule. Suitable plasmids for these embodiments include pSR1 and other derivatives of pSR1 (Archer, J. et al., *J. Gen. Microbiol.* 139: 1753-1759 (1993)).

For various embodiments of the invention drawn to a method to increase production of L-lysine, screening for increased production of L-lysine, can be determined by directly comparing the amount of L-lysine produced in culture by a *Corynebacterium* species host strain to that of a *Corynebacterium* species transformed host strain in which lysine biosynthesis gene or genes are amplified. The level of production of lysine can conveniently be determined by the following formula to calculate the percent yield from dextrose: [(g lysine/L/(g dextrose consumed/L)]*100.

In one embodiment, the invention provides a method to increase the production of lysine comprising: (a) transforming a host cell with an isolated KDBH polynucleotide molecule (b) selecting a transformed host cell; and (c) screening for increased production of lysine from said transformed host cell relative to said host cell. In another embodiment of the method, the method further comprises growing said transformed host cell in a medium; and purifying lysine produced by said transformed host cell.

A variety of media known to those skilled in the art can be used to support cell growth for the production of lysine. Illustrative examples of suitable carbon sources include, but are not limited to: carbohydrates, such as glucose, fructose, sucrose, starch hydrolysate, cellulose hydrolysate and molasses; organic acids, such as acetic acid, propionic acid, formic acid, malic acid, citric acid, and fumaric acid; and alcohols, such as glycerol. Illustrative examples of suitable nitrogen sources include, but are not limited to: ammonia, including ammonia gas and aqueous ammonia; ammonium salts of inorganic or organic acids, such as ammonium chloride, ammonium phosphate, ammonium sulfate and ammonium acetate; and other nitrogen-containing sources, including meat extract, peptone, corn steep liquor, casein hydrolysate, soybean cake hydrolysate, urea and yeast extract.

A variety of fermentation techniques are known in the art which can be employed in processes of the invention drawn to the production of amino acids. Generally, amino acids can be commercially produced from the invention in fermentation processes such as the batch type or of the fed-batch type. In batch type fermentations, all nutrients are added at the beginning of the fermentation. In fed-batch or extended fed-batch type fermentations one or a number of nutrients are continuously supplied to the culture, right from the beginning of the fermentation or after the culture has reached a certain age, or when the nutrient(s) which are fed were exhausted from the culture fluid. A variant of the extended batch of fed-batch type fermentation is the repeated fed-batch or fill-and-draw fermentation, where part of the contents of the fermenter is removed at some time, for instance when the fermenter is full, while feeding of a nutrient is continued. In this way a fermentation can be extended for a longer time.

Another type of fermentation, the continuous fermentation or chemostat culture, uses continuous feeding of a complete medium, while culture fluid is continuously or semi-continuously withdrawn in such a way that the volume of the broth in the fermenter remains approximately constant. A continuous fermentation can in principle be maintained for an infinite time.

In a batch fermentation an organism grows until one of the essential nutrients in the medium becomes exhausted, or until fermentation conditions become unfavorable (e.g., the pH decreases to a value inhibitory for microbial growth). In fed-batch fermentations measures are normally taken to maintain favorable growth conditions, e.g., by using pH control, and exhaustion of one or more essential nutrients is prevented by feeding these nutrient(s) to the culture. The microorganism will continue to grow, at a growth rate dictated by the rate of nutrient feed. Generally a single nutrient, very often the carbon source, will become limiting for growth. The same principle applies for a continuous fermentation, usually one nutrient in the medium feed is limiting, all other nutrients are in excess. The limiting nutrient will be present in the culture fluid at a very low concentration, often unmeasurably low. Different types of nutrient limitation can be employed. Carbon source limitation is most often used. Other examples are limitation by the nitrogen source, limitation by oxygen, limitation by a specific nutrient such as a vitamin or an amino acid (in case the microorganism is auxotrophic for such a compound), limitation by sulphur and limitation by phosphorous.

Lysine can be recovered by any method known in the art. Exemplary procedures are provided in the following: Van Walsem, H. J. & Thompson, M. C., *J. Biotechnol.* 59:127-132 (1997), and U.S. Pat. No. 3,565,951, both of which are incorporated herein by reference.

The pDElia2$_{FC5}$-KDB, the pK184-KDBH, the pDElia2$_{FC5}$-KDB2 and the pDElia2$_{FC5}$-KDB2HL constructs in NRRL-B11474 host cells were deposited at an acceptable International Depositary Authority in accordance with the Budapest Treaty on the International Recognition of the Deposit of Microorganisms for the Purposes of Patent Procedure. The deposits have been made with the Agricultural Research Service, Culture Collection (NRRL), 1815 North University Street, Peoria, Ill. 61604.

All patents and publications referred to herein are expressly incorporated by reference in their entirety.

EXAMPLES

Example 1

Preparation of L-Lysine Pathway Multi-Gene Constructs

Constructs comprising a KDB, a KDBH, a KDB2HL or a KDB2 polynucleotide molecule were made from the following sources:

| Gene(s) | Source |
| --- | --- |
| ask-asd | Strain ATCC 21529; |
| dapB | Strain NRRL B11474; |
| ddh | Strain NRRL B11474; |
| ORF2 | Strain NRRL B11474; |
| lysA | Strain ASO19; |
| Promoter | |
| P1 | argS-lysA operon from pRS6 |

The polymerase chain reaction (PCR) technique was used to construct the KDB, KDBH, KDB2, and KDBHL constructs. Standard PCR and subcloning procedures were utilized in cloning the coding regions of ask-asd, dapB-ORF2-dapA, ddh.

The primers utilized for cloning experiments included:

| Primer name | Sequence |
| --- | --- |
| ask (SEQ ID NO: 17) | 5'-GGGTACCTCGCGAAGTAGCACCTGTCAC-3' |
| asd (SEQ ID NO: 18) | 5'-GCGGATCCCCCATCGCCCCTCAAAGA-3' |
| dapB (SEQ ID NO: 19) | 5'-AACGGGCGGTGAAGGGCAACT-3' |
| ORF2 (SEQ ID NO: 25) | 5'-GCTCATAGAGTTCAAGGTTACCTTCTTCCC-3' |
| ddh1 (SEQ ID NO: 21) | 5'-CCATGGTACCAAGTGCGTGGCGAG-3' |
| ddh2 (SEQ ID NO: 22) | 5'-CCATGGTACCACACTGTTTCCTTGC-3' |
| lysA$_{(ATG)}$ (SEQ ID NO: 23) | 5'-CCGGAGAAGATGTAACAATGGCTAC-3' |
| lysA3B (SEQ ID NO: 24) | 5'-CCTCGACTGCAGACCCCTAGACACC-3' |
| dapA (SEQ ID NO: 20) | 5'-TGAAAGACAGGGGTATCCAGA-3' |

Construction procedures and intermediate plasmids are described in FIGS. 11-14. The following steps (FIG. 11) were performed in constructing the pDElia2$_{FC5}$-KDB vector:

1. pGEMT-ask-asd: an approximately 2.6 Kb PCR product containing the ask-asd operon of ATCC21529 using primers ask and asd was cloned into pGEM-T (Promega pGEM-T vector systems).
2. pFC3-ask-asd: an approximately 2.6 Kb NsiI-ApaI fragment of pGEMT-ask-asd was cloned into pFC3 cut with PstI and ApaI.
3. pFC3-dapB-ORF2-dapA: an approximately 2.9 Kb PCR product of NRRL-B11474 dapB-ORF2-dapA coding region was cloned into pFC3 at the EcoRV site.
4. pFC3-dapB: the large ClaI fragment of pFC3-dapB-ORF2-dapA was religated.
5. pUC18-ddh: an approximately 1.3 Kb KpnI fragment of pADM21 containing ddh (NRRL-B11474 locus) was subcloned into pUC18 at the KpnI site.
6. pFC1-ddh: an approximately 1.3 Kb SalI-EcoRI fragment of pUC18-ddh was cloned into pFC1 cut with SalI and EcoRI.
7. pFC1-ddh-lysA: an approximately 2.1 Kb EcoRI-PstI fragment (containing the intact lysA DNA) of pRS6 was cloned into pFC1-ddh cut with EcoRI and PstI.
8. pFC1-ask-asd-ddh-lysA: an approximately 2.6 Kb SwaI-FseI fragment of pFC3-ask-asd was cloned into pFC1-ddh-lysA cut with SwaI and FseI.
9. pFC3-ask-asd-dapB-ddh-lysA: an approximately 6 Kb SpeI fragment of pFC1-ask-asd-ddh-lysA was cloned into pFC3-dapB at the SpeI site.
10. pDElia2$_{FC5}$-ask-asd-dapB-ddh-lysA (pDElia2$_{FC5}$-KDBHL): an approximately 7.38 Kb NotI-PmeI fragment of pFC3-ask-asd-dapB-ddh-lysA was cloned into pDElia$^2$$_{FC5}$ cut with NotI and PmeI.
11. pDElia2: an approximately 1.24 Kb blunted PstI fragment of pUC4K was ligated with the approximately 1.75 Kb DraI-SspI fragment of pUC19.
12. pDElia2$_{FC5}$: the small PvuII fragment of pFC5 was ligated with the large PvuII fragment of pDElia2.
13. pDElia2$_{FC5}$-ask-asd-dapB (pDElia2$_{FC5}$-KDB): an approximately 4 Kb ApaI fragment of pDElia2$_{FC5}$-KDBHL was cloned into pDElia2$_{FC5}$ at the ApaI site.

*Corynebacterium* (NRRL-B11474) containing the pDElia2$_{FC5}$-KDB construct was deposited at an acceptable International Depositary Authority in accordance with the Budapest Treaty on the International Recognition of the Deposit of Microorganisms for the Purposes of Patent Procedure. The deposit has been made with the Agricultural Research Service, Culture Collection (NRRL), 1815 North University Street, Peoria, Ill. 61604 on Feb. 1, 2001. The deposit is numbered NRRL-B30458.

The following steps (FIG. 12) were preformed in constructing the pK184-KDBH construct:

1. pGEMT-ask-asd: an approximately 2.6 Kb PCR product containing the ask-asd operon of ATCC21529 using primers ask and asd was cloned into pGEM-T (Promega pGEM-T vector systems).
2. pFC3-ask-asd: an approximately 2.6 Kb NsiI-ApaI fragment of pGEMT-ask-asd was cloned into pFC3 cut with PstI and ApaI.
3. pFC3-ask-asd-ddh: an approximately 1.3 Kb KpnI fragment containing NRRL-B11474 ddh was cloned into pFC3-ask-asd at the KpnI site.
4. pFC3-dapB-ORF2-dapA: an approximately 2.9 Kb PCR product of NRRL-B11474 dapB-ORF2-dapA coding region was cloned into pFC3 at the EcoRV site.
5. pFC3-dapB: the large ClaI fragment of pFC3-dapB-ORF2-dapA was religated.
6. pFC3-ask-asd-dapB-ddh: an approximately 4 Kb NotI-SwaI fragment of pFC3-ask-asd-ddh was cloned into pFC3-dapB digested with NotI and SmaI.
7. pK184-ask-asd-dapB-ddh (pK184-KDBH): an approximately 5.3 Kb PmeI fragment containing ask-asd-dapB-ddh was cloned into pK184 at the SmaI site.

*Corynebacterium* (NRRL-B11474) containing the pK184-KDBH construct was deposited at an acceptable International Depositary Authority in accordance with the Budapest Treaty on the International Recognition of the Deposit of Microorganisms for the Purposes of Patent Procedure. The deposit has been made with the Agricultural Research Service, Culture Collection (NRRL), 1815 North University Street, Peoria, Ill. 61604 on Feb. 1, 2001. The deposit is numbered NRRL-B30410.

The following steps (FIG. 13) were performed in constructing the pDElia2$_{FC5}$-KDB2 vector:

1. pGEMT-ask-asd: an approximately 2.6 Kb PCR product containing the ask-asd operon of ATCC21529 using primers ask and asd was cloned into pGEM-T (Promega pGEM-T vector systems).
2. pUC18-ddh: an approximately 1.3 Kb KpnI fragment of pADM21 containing ddh (BF100 locus) was subcloned into pUC18 at the KpnI site.
3. pFC3-ask-asd: an approximately 2.6 Kb NsiI-ApaI fragment of pGEMT-ask-asd was cloned into pFC3 cut with PstI and ApaI
4. pFC1-dapB-ORF2: an approximately 2 Kb PCR product of NRRL-B11474 dapB-ORF2 coding region was cloned into pFC1 at the EcoRV site.
5. pFC1-ddh: an approximately 1.3 Kb PstI-EcoRI fragment of pUC18-ddh was cloned into pFC1 cut with PstI and EcoRI.
6. pUC19-P1: an approximately 550 bp HpaI-PvuII fragment (containing the first promoter, P1, of the argS-lysA operon) of pRS6 was cloned into pUC19 at the SmaI site.
7. pUC19-P1lysA: an approximately 1.45 Kb promoterless PCR product, using primers LysA(ATG) and LysA3B, of ASO19 lysA coding region is cloned into pUC19-P1 at the HincII site.

8. pFC1-P1lysA: an approximately 2 Kb EcoRI-HindIII fragment of pUC19-P1lysA was cloned in to pFC1 cut with EcoRI and HindIII.

9. pFC1-ddh-P1lysA: an approximately 1.3 Kb EcoRI-NotI fragment of pFC1-ddh was cloned into pFC1-P1lysA cut with EcoRI and NotI.

10. pFC1-ask-asd-ddh-P1lysA: an approximately 2.6 Kb SwaI-FseI fragment of pFC3-asd-asd was cloned into pFC1-ddh-P1lysA cut with SwaI and FseI.

10. pFC1-ask-asd-dapB-ORF2-ddh-P1lysA (pFC1-KDB2HPIL): an approximately 5.9 Kb SpeI fragment of pFC1-ask-asd-ddh-P1lysA was cloned into pFC1-dapB-ORF2 at the SpeI site.

11. pDElia2$_{FCS}$: the small PvuII fragment of pFC5 was ligated with the large PvuII fragment of pDElia2.

12. pDElia2$_{FCS}$-ask-asd-dapB-ORF2 (pDElia2$_{FCS}$-KDB2): an approximately 4.7 Kb ApaI fragment containing KDB2 of pFC1-KDB2HP1L was cloned into pDElia2$_{FCS}$ at the ApaI site.

*Corynebacterium* (NRRL-B11474) containing the pDElia2$_{FCS}$-KDB2 construct was deposited at an acceptable International Depositary Authority in accordance with the Budapest Treaty on the International Recognition of the Deposit of Microorganisms for the Purposes of Patent Procedure. The deposit has been made with the Agricultural Research Service, Culture Collection (NRRL), 1815 North University Street, Peoria, Ill. 61604 on Feb. 1, 2001. The deposit is numbered NRRL-B30459.

The following steps (FIG. 14) were performed in constructing the pDElia2$_{FCS}$-KDB2HP1L vector:

1. pGEMT-ask-asd: an approximately 2.6 Kb PCR product containing the ask-asd operon of ATCC21529 using primers ask and asd was cloned into pGEM-T (Promega pGEM-T vector systems).

2. pUC18-ddh: an approximately 1.3 Kb KpnI fragment of pADM21 containing ddh (NRRL-B11474 locus) was subcloned into pUC18 at the KpnI site.

3. pFC3-ask-asd: an approximately 2.6 Kb NsiI-ApaI fragment of pGEMT-ask-asd was cloned into pFC3 cut with PstI and ApaI.

4. pFC1-dapB-ORF2: an approximately 2 Kb PCR product of NRRL-B11474 dapB-ORF2 coding region was cloned into pFC1 at the EcoRV site.

5. pFC1-ddh: an approximately 1.3 Kb PstI-EcoRI fragment of pUC19-ddh was cloned into pFC1 cut with PstI and EcoRI.

6. pUC19-P1: an approximately 550 bp HpaI-PvuII fragment (containing the first promoter, P1, of the argS-lysA operon) of pRS6 was cloned into pUC19 at the SmaI site.

7. pUC19-P1lysA: an approximately 1.45 Kb promoterless PCR product, using primers LysA(ATG) and LysA3B, of ASO19 lysA coding region is cloned into pUC19-P1 at the HincII site.

8. pFC1-P1lysA: an approximately 2 Kb EcoRI-HindIII fragment of pUC19-P1lysA was cloned into pFC1 cut with EcoRI and HindIII.

9. pFC1-ddh-P1lysA: an approximately 1.3 Kb EcoRI-NotI fragment of pFC1-ddh was cloned into pFC1-P1lysA cut with EcoRI and NotI.

10. pFC1-ask-asd-ddh-P1lysA: an approximately 2.6 Kb SwaI-FseI fragment of pFC3-ask-asd was cloned into pFC1-ddh-P1lysA cut with SwaI and FseI.

11. pFC1-ask-asd-dapB-ORF2-ddh-P1lysA (pFC1-KDB2HPIL): an approximately 5.9 Kb SpeI fragment of pFC1-ask-asd-ddh-P1lysA was cloned into pFC1-dapB-ORF2 at the SpeI site.

12. pDElia2$_{FCS}$: the small PvuII fragment of pFC5 was ligated with the large PvuII fragment of pDElia2

13. pDElia2$_{FCS}$-ask-asd-dapB-ORF2-ddh-P1lysA (pDElia2$_{FCS}$-KDB2HP1L): an approximately 7.9 Kb NHE fragment of pFC1-ask-asd-dapB-ORF2-ddh-P1lysA was cloned into pDElia2$_{FCS}$ at the NHE site.

*Corynebacterium* (NRRL-B11474) containing the pDElia2$_{FCS}$-KDB2HP1L construct was deposited at an acceptable International Depositary Authority in accordance with the Budapest Treaty on the International Recognition of the Deposit of Microorganisms for the Purposes of Patent Procedure. The deposit has been made with the Agricultural Research Service, Culture Collection (NRRL), 1815 North University Street, Peoria, Ill. 61604 on Feb. 1, 2001. The deposit is numbered NRRL-B30522.

Example 2

Screening and Selection of Strains with Improved L-Lysine Production

The production of L-lysine by cells stably transformed with multi-gene constructs is summarized in Table 1.

TABLE 1

Lysine production by various parental and stably transfected bacteria

| Strain Tested | lysine titer (g/L) | L-lysine yield (%) | Cell Deposit |
|---|---|---|---|
| NRRL-B11474 | 31 | 30 | |
| NRRL-B11474::pDElia2$_{FCS}$-KDB | 34 | 37 | NRRL-B30458 |
| NRRL-B11474 | 31 | 31 | |
| NRRL-B11474::pK184-KDBH | 38 | 37.4 | NRRL-B30410 |
| NRRL-B11474 | 30 | 30 | |
| NRRL-B11474::pDElia2$_{FCS}$-KDB2 | 39 | 37 | NRRL-B30459 |
| NRRL-B11474 | 31 | 33 | |
| NRRL-B11474::pDElia2$_{FCS}$-KDB2HP1L | 38 | 41 | NRRL-B30522 |

* * * * *

Having now fully described the present invention in some detail by way of illustration and example for purposes of clarity of understanding, it will be obvious to one of ordinary skill in the art that same can be performed by modifying or changing the invention with a wide and equivalent range of conditions, formulations and other parameters thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

SEQUENCE LISTING

<160> NUMBER OF SEQ ID NOS: 25

<210> SEQ ID NO 1
<211> LENGTH: 1266
<212> TYPE: DNA
<213> ORGANISM: Corynebacterium glutamicum
<220> FEATURE:
<221> NAME/KEY: CDS
<222> LOCATION: (1)..(1266)

<400> SEQUENCE: 1

| | | | | | | | | | | | | | | | | |
|---|---|---|---|---|---|---|---|---|---|---|---|---|---|---|---|---|
| gtg | gcc | ctg | gtc | gta | cag | aaa | tat | ggc | ggt | tcc | tcg | ctt | gag | agt | gcg | 48 |
| Met | Ala | Leu | Val | Val | Gln | Lys | Tyr | Gly | Gly | Ser | Ser | Leu | Glu | Ser | Ala | |
| 1 | | | | 5 | | | | | 10 | | | | | 15 | | |
| gaa | cgc | att | aga | aac | gtc | gct | gaa | cgg | atc | gtt | gcc | acc | aag | aag | gct | 96 |
| Glu | Arg | Ile | Arg | Asn | Val | Ala | Glu | Arg | Ile | Val | Ala | Thr | Lys | Lys | Ala | |
| | | | 20 | | | | | 25 | | | | | 30 | | | |
| gga | aat | gat | gtc | gtg | gtt | gtc | tgc | tcc | gca | atg | gga | gac | acc | acg | gat | 144 |
| Gly | Asn | Asp | Val | Val | Val | Val | Cys | Ser | Ala | Met | Gly | Asp | Thr | Thr | Asp | |
| | | 35 | | | | | 40 | | | | | 45 | | | | |
| gaa | ctt | cta | gaa | ctt | gca | gcg | gca | gtg | aat | ccc | gtt | ccg | cca | gct | cgt | 192 |
| Glu | Leu | Leu | Glu | Leu | Ala | Ala | Ala | Val | Asn | Pro | Val | Pro | Pro | Ala | Arg | |
| | 50 | | | | | 55 | | | | | 60 | | | | | |
| gaa | atg | gat | atg | ctc | ctg | act | gct | ggt | gag | cgt | att | tct | aac | gct | ctc | 240 |
| Glu | Met | Asp | Met | Leu | Leu | Thr | Ala | Gly | Glu | Arg | Ile | Ser | Asn | Ala | Leu | |
| 65 | | | | 70 | | | | | 75 | | | | | 80 | | |
| gtc | gcc | atg | gct | att | gag | tcc | ctt | ggc | gca | gaa | gct | caa | tct | ttc | act | 288 |
| Val | Ala | Met | Ala | Ile | Glu | Ser | Leu | Gly | Ala | Glu | Ala | Gln | Ser | Phe | Thr | |
| | | | 85 | | | | | 90 | | | | | 95 | | | |
| ggc | tct | cag | gct | ggt | gtg | ctc | acc | acc | gag | cgc | cac | gga | aac | gca | cgc | 336 |
| Gly | Ser | Gln | Ala | Gly | Val | Leu | Thr | Thr | Glu | Arg | His | Gly | Asn | Ala | Arg | |
| | | | 100 | | | | | 105 | | | | | 110 | | | |
| att | gtt | gac | gtc | aca | ccg | ggt | cgt | gtg | cgt | gaa | gca | ctc | gat | gag | ggc | 384 |
| Ile | Val | Asp | Val | Thr | Pro | Gly | Arg | Val | Arg | Glu | Ala | Leu | Asp | Glu | Gly | |
| | | | 115 | | | | | 120 | | | | | 125 | | | |
| aag | atc | tgc | att | gtt | gct | ggt | ttt | cag | ggt | gtt | aat | aaa | gaa | acc | cgc | 432 |
| Lys | Ile | Cys | Ile | Val | Ala | Gly | Phe | Gln | Gly | Val | Asn | Lys | Glu | Thr | Arg | |
| | 130 | | | | | 135 | | | | | 140 | | | | | |
| gat | gtc | acc | acg | ttg | ggt | cgt | ggt | ggt | tct | gac | acc | act | gca | gtt | gcg | 480 |
| Asp | Val | Thr | Thr | Leu | Gly | Arg | Gly | Gly | Ser | Asp | Thr | Thr | Ala | Val | Ala | |
| 145 | | | | 150 | | | | | 155 | | | | | 160 | | |
| ttg | gca | gct | gct | ttg | aac | gct | gat | gtg | tgt | gag | att | tac | tcg | gac | gtt | 528 |
| Leu | Ala | Ala | Ala | Leu | Asn | Ala | Asp | Val | Cys | Glu | Ile | Tyr | Ser | Asp | Val | |
| | | | 165 | | | | | 170 | | | | | 175 | | | |
| gac | ggt | gtg | tat | acc | gct | gac | ccg | cgc | atc | gtt | cct | aat | gca | cag | aag | 576 |
| Asp | Gly | Val | Tyr | Thr | Ala | Asp | Pro | Arg | Ile | Val | Pro | Asn | Ala | Gln | Lys | |
| | | | 180 | | | | | 185 | | | | | 190 | | | |
| ctg | gaa | aag | ctc | agc | ttc | gaa | gaa | atg | ctg | gaa | ctt | gct | gct | gtt | ggc | 624 |
| Leu | Glu | Lys | Leu | Ser | Phe | Glu | Glu | Met | Leu | Glu | Leu | Ala | Ala | Val | Gly | |
| | | 195 | | | | | 200 | | | | | 205 | | | | |
| tcc | aag | att | ttg | gtg | ctg | cgc | agt | gtt | gaa | tac | gct | cgt | gca | ttc | aat | 672 |
| Ser | Lys | Ile | Leu | Val | Leu | Arg | Ser | Val | Glu | Tyr | Ala | Arg | Ala | Phe | Asn | |
| | 210 | | | | | 215 | | | | | 220 | | | | | |
| gtg | cca | ctt | cgc | gta | cgc | tcg | tct | tat | agt | aat | gat | ccc | ggc | act | ttg | 720 |
| Val | Pro | Leu | Arg | Val | Arg | Ser | Ser | Tyr | Ser | Asn | Asp | Pro | Gly | Thr | Leu | |
| 225 | | | | 230 | | | | | 235 | | | | | 240 | | |

-continued

| | | |
|---|---|---|
| att gcc ggc tct atg gag gat att cct gtg gaa gaa gca gtc ctt acc<br>Ile Ala Gly Ser Met Glu Asp Ile Pro Val Glu Glu Ala Val Leu Thr<br>245 250 255 | | 768 |
| ggt gtc gca acc gac aag tcc gaa gcc aaa gta acc gtt ctg ggt att<br>Gly Val Ala Thr Asp Lys Ser Glu Ala Lys Val Thr Val Leu Gly Ile<br>260 265 270 | | 816 |
| tcc gat aag cca ggc gag gct gcc aag gtt ttc cgt gcg ttg gct gat<br>Ser Asp Lys Pro Gly Glu Ala Ala Lys Val Phe Arg Ala Leu Ala Asp<br>275 280 285 | | 864 |
| gca gaa atc aac att gac atg gtt ctg cag aac gtc tcc tct gtg gaa<br>Ala Glu Ile Asn Ile Asp Met Val Leu Gln Asn Val Ser Ser Val Glu<br>290 295 300 | | 912 |
| gac ggc acc acc gac atc acg ttc acc tgc cct cgc gct gac gga cgc<br>Asp Gly Thr Thr Asp Ile Thr Phe Thr Cys Pro Arg Ala Asp Gly Arg<br>305 310 315 320 | | 960 |
| cgt gcg atg gag atc ttg aag aag ctt cag gtt cag ggc aac tgg acc<br>Arg Ala Met Glu Ile Leu Lys Lys Leu Gln Val Gln Gly Asn Trp Thr<br>325 330 335 | | 1008 |
| aat gtg ctt tac gac gac cag gtc ggc aaa gtc tcc ctc gtg ggt gct<br>Asn Val Leu Tyr Asp Asp Gln Val Gly Lys Val Ser Leu Val Gly Ala<br>340 345 350 | | 1056 |
| ggc atg aag tct cac cca ggt gtt acc gca gag ttc atg gaa gct ctg<br>Gly Met Lys Ser His Pro Gly Val Thr Ala Glu Phe Met Glu Ala Leu<br>355 360 365 | | 1104 |
| cgc gat gtc aac gtg aac atc gaa ttg att tcc atc tct gag atc cgc<br>Arg Asp Val Asn Val Asn Ile Glu Leu Ile Ser Ile Ser Glu Ile Arg<br>370 375 380 | | 1152 |
| att tcc gtg ctg atc cgt gaa gat gat ctg gat gct gct gca cgt gca<br>Ile Ser Val Leu Ile Arg Glu Asp Asp Leu Asp Ala Ala Ala Arg Ala<br>385 390 395 400 | | 1200 |
| ttg cat gag cag ttc cag ctg ggc ggc gaa gac gaa gcc gtc gtt tat<br>Leu His Glu Gln Phe Gln Leu Gly Gly Glu Asp Glu Ala Val Val Tyr<br>405 410 415 | | 1248 |
| gca ggc acc gga cgc taa<br>Ala Gly Thr Gly Arg<br>420 | | 1266 |

<210> SEQ ID NO 2
<211> LENGTH: 421
<212> TYPE: PRT
<213> ORGANISM: Corynebacterium glutamicum

<400> SEQUENCE: 2

Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

-continued

```
Lys Ile Cys Ile Val Ala Gly Phe Gln Gly Val Asn Lys Glu Thr Arg
            130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
290                 295                 300

Asp Gly Thr Thr Asp Ile Thr Phe Thr Cys Pro Arg Ala Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Ile Ser Glu Ile Arg
370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420

<210> SEQ ID NO 3
<211> LENGTH: 1035
<212> TYPE: DNA
<213> ORGANISM: Corynebacterium glutamicum
<220> FEATURE:
<221> NAME/KEY: CDS
<222> LOCATION: (1)..(1035)

<400> SEQUENCE: 3 atg acc acc atc gca gtt gtt ggt gca acc ggc cag gtc ggc cag gtt      48
Met Thr Thr Ile Ala Val Val Gly Ala Thr Gly Gln Val Gly Gln Val
1               5                   10                  15 atg cgc acc ttt ttg gaa gag cgc aat ttc cca gct gac act gtt cgt      96
Met Arg Thr Phe Leu Glu Glu Arg Asn Phe Pro Ala Asp Thr Val Arg
                20                  25                  30 ttc ttt gct tcc ccg cgt tcc gca ggc cgt aag att gaa ttc cgt ggc     144
Phe Phe Ala Ser Pro Arg Ser Ala Gly Arg Lys Ile Glu Phe Arg Gly
            35                  40                  45
```

| | |
|---|---|
| acg gaa atc gag gta gaa gac att act cag gca acc gag gag tcc ctc<br>Thr Glu Ile Glu Val Glu Asp Ile Thr Gln Ala Thr Glu Glu Ser Leu<br>50                      55                      60 | 192 |
| aag ggc atc gac gtt gcg ttg ttc tct gct gga ggc acc gct tcc aag<br>Lys Gly Ile Asp Val Ala Leu Phe Ser Ala Gly Gly Thr Ala Ser Lys<br>65                      70                      75                      80 | 240 |
| cag tac gct cca ctg ttt gct gct gca ggc gcg act gtt gtg gat aac<br>Gln Tyr Ala Pro Leu Phe Ala Ala Ala Gly Ala Thr Val Val Asp Asn<br>                        85                      90                      95 | 288 |
| tct tct gct tgg cgc aag gac gac gag gtt cca cta atc gtc tct gag<br>Ser Ser Ala Trp Arg Lys Asp Asp Glu Val Pro Leu Ile Val Ser Glu<br>                100                    105                    110 | 336 |
| gtg aac cct tcc gac aag gat tcc ctg gtc aag ggc att att gcg aat<br>Val Asn Pro Ser Asp Lys Asp Ser Leu Val Lys Gly Ile Ile Ala Asn<br>            115                    120                    125 | 384 |
| cct aac tgc acc acc atg gct gca atg cca gtg ctg aag cca ctg cac<br>Pro Asn Cys Thr Thr Met Ala Ala Met Pro Val Leu Lys Pro Leu His<br>130                      135                    140 | 432 |
| gat gcc gct ggt ctt gta aag ctt cac gtt tcc tct tac cag gct gtt<br>Asp Ala Ala Gly Leu Val Lys Leu His Val Ser Ser Tyr Gln Ala Val<br>145                      150                    155                    160 | 480 |
| tcc ggt tct ggt ctt gca ggt gtg gaa acc ttg gca aag cag gtt gct<br>Ser Gly Ser Gly Leu Ala Gly Val Glu Thr Leu Ala Lys Gln Val Ala<br>                      165                    170                    175 | 528 |
| gca gtt ggc gac cac aac gtt gag ttc gtc cat gat gga cag gct gct<br>Ala Val Gly Asp His Asn Val Glu Phe Val His Asp Gly Gln Ala Ala<br>                180                    185                    190 | 576 |
| gac gca ggc gat gtc gga cct tac gtt tcc cca atc gct tac aac gtg<br>Asp Ala Gly Asp Val Gly Pro Tyr Val Ser Pro Ile Ala Tyr Asn Val<br>            195                    200                    205 | 624 |
| ctg cca ttc gcc gga aac ctc gtc gat gac ggc acc ttc gaa acc gac<br>Leu Pro Phe Ala Gly Asn Leu Val Asp Asp Gly Thr Phe Glu Thr Asp<br>210                      215                    220 | 672 |
| gaa gag cag aag ctg cgc aac gaa tcc cgc aag att ctc ggc ctc cca<br>Glu Glu Gln Lys Leu Arg Asn Glu Ser Arg Lys Ile Leu Gly Leu Pro<br>225                      230                    235                    240 | 720 |
| gac ctc aag gtc tca ggc acc tgc gtc cgc gtg ccg gtt ttc acc ggc<br>Asp Leu Lys Val Ser Gly Thr Cys Val Arg Val Pro Val Phe Thr Gly<br>                      245                    250                    255 | 768 |
| cac acg ctg acc att cac gcc gaa ttc gac aag gca atc acc gtc gag<br>His Thr Leu Thr Ile His Ala Glu Phe Asp Lys Ala Ile Thr Val Glu<br>                260                    265                    270 | 816 |
| cag gcg cag gag atc ttg ggt gcc gct tca ggc gtc gag ctt gtc gac<br>Gln Ala Gln Glu Ile Leu Gly Ala Ala Ser Gly Val Glu Leu Val Asp<br>            275                    280                    285 | 864 |
| gtc cca acc cca ctt gca gct gcc ggc att gac gaa tcc ctc gtt gga<br>Val Pro Thr Pro Leu Ala Ala Ala Gly Ile Asp Glu Ser Leu Val Gly<br>290                      295                    300 | 912 |
| cgc atc cgt cag gac tcc act gtc gac gac aac cgc ggt ctg gtt ctc<br>Arg Ile Arg Gln Asp Ser Thr Val Asp Asp Asn Arg Gly Leu Val Leu<br>305                      310                    315                    320 | 960 |
| gtc gta tct ggc gat aac ctt cgc aag ggc gca gca ctg aac acc att<br>Val Val Ser Gly Asp Asn Leu Arg Lys Gly Ala Ala Leu Asn Thr Ile<br>                      325                    330                    335 | 1008 |
| cag att gct gag ctg ctg gtt aag taa<br>Gln Ile Ala Glu Leu Leu Val Lys<br>            340 | 1035 |

<210> SEQ ID NO 4
<211> LENGTH: 344
<212> TYPE: PRT

<213> ORGANISM: Corynebacterium glutamicum

<400> SEQUENCE: 4

Met Thr Thr Ile Ala Val Val Gly Ala Thr Gly Gln Val Gly Gln Val
1               5                   10                  15

Met Arg Thr Phe Leu Glu Glu Arg Asn Phe Pro Ala Asp Thr Val Arg
            20                  25                  30

Phe Phe Ala Ser Pro Arg Ser Ala Gly Arg Lys Ile Glu Phe Arg Gly
        35                  40                  45

Thr Glu Ile Glu Val Glu Asp Ile Thr Gln Ala Thr Glu Glu Ser Leu
    50                  55                  60

Lys Gly Ile Asp Val Ala Leu Phe Ser Ala Gly Gly Thr Ala Ser Lys
65                  70                  75                  80

Gln Tyr Ala Pro Leu Phe Ala Ala Gly Ala Thr Val Val Asp Asn
                85                  90                  95

Ser Ser Ala Trp Arg Lys Asp Glu Val Pro Leu Ile Val Ser Glu
            100                 105                 110

Val Asn Pro Ser Asp Lys Asp Ser Leu Val Lys Gly Ile Ile Ala Asn
            115                 120                 125

Pro Asn Cys Thr Thr Met Ala Ala Met Pro Val Leu Lys Pro Leu His
130                 135                 140

Asp Ala Ala Gly Leu Val Lys Leu His Val Ser Ser Tyr Gln Ala Val
145                 150                 155                 160

Ser Gly Ser Gly Leu Ala Gly Val Glu Thr Leu Ala Lys Gln Val Ala
                165                 170                 175

Ala Val Gly Asp His Asn Val Glu Phe Val His Asp Gly Gln Ala Ala
            180                 185                 190

Asp Ala Gly Asp Val Gly Pro Tyr Val Ser Pro Ile Ala Tyr Asn Val
        195                 200                 205

Leu Pro Phe Ala Gly Asn Leu Val Asp Asp Gly Thr Phe Glu Thr Asp
    210                 215                 220

Glu Glu Gln Lys Leu Arg Asn Glu Ser Arg Lys Ile Leu Gly Leu Pro
225                 230                 235                 240

Asp Leu Lys Val Ser Gly Thr Cys Val Arg Val Pro Val Phe Thr Gly
                245                 250                 255

His Thr Leu Thr Ile His Ala Gly Phe Asp Lys Ala Ile Thr Val Glu
            260                 265                 270

Gln Ala Gln Glu Ile Leu Gly Ala Ala Ser Gly Val Glu Leu Val Asp
        275                 280                 285

Val Pro Thr Pro Leu Ala Ala Ala Gly Ile Asp Glu Ser Leu Val Gly
    290                 295                 300

Arg Ile Arg Gln Asp Ser Thr Val Asp Asp Asn Arg Gly Leu Val Leu
305                 310                 315                 320

Val Val Ser Gly Asp Asn Leu Arg Lys Gly Ala Ala Leu Asn Thr Ile
                325                 330                 335

Gln Ile Ala Glu Leu Leu Val Lys
            340

<210> SEQ ID NO 5
<211> LENGTH: 747
<212> TYPE: DNA
<213> ORGANISM: Corynebacterium glutamicum
<220> FEATURE:
<221> NAME/KEY: CDS
<222> LOCATION: (1)..(747)

<400> SEQUENCE: 5

```
atg gga atc aag gtt ggc gtt ctc gga gcc aaa ggc cgt gtt ggt caa      48
Met Gly Ile Lys Val Gly Val Leu Gly Ala Lys Gly Arg Val Gly Gln
1               5                   10                  15 act att gtg gca gca gtc aat gag tcc gac gat ctg gag ctt gtt gca      96
Thr Ile Val Ala Ala Val Asn Glu Ser Asp Asp Leu Glu Leu Val Ala
            20                  25                  30 gag atc ggc gtc gac gat gat ttg agc ctt ctg gta gac aac ggc gct     144
Glu Ile Gly Val Asp Asp Asp Leu Ser Leu Leu Val Asp Asn Gly Ala
        35                  40                  45 gaa gtc gtc gtt gac ttc acc act cct aac gct gtg atg ggc aac ctg     192
Glu Val Val Val Asp Phe Thr Thr Pro Asn Ala Val Met Gly Asn Leu
    50                  55                  60 gag ttc tgc atc aac aac ggc att tct gcg gtt gtt gga acc acg ggc     240
Glu Phe Cys Ile Asn Asn Gly Ile Ser Ala Val Val Gly Thr Thr Gly
65                  70                  75                  80 ttc gat aat gct cgt ttg gag cag gtt cgc gcc tgg ctt gaa gga aaa     288
Phe Asp Asn Ala Arg Leu Glu Gln Val Arg Ala Trp Leu Glu Gly Lys
                85                  90                  95 gac aat gtc ggt gtt ctg atc gca cct aac ttt gct atc tct gcg gtg     336
Asp Asn Val Gly Val Leu Ile Ala Pro Asn Phe Ala Ile Ser Ala Val
            100                 105                 110 ttg acc atg gtc ttt tcc aag cag gct gcc cgc ttc ttc gaa tca gct     384
Leu Thr Met Val Phe Ser Lys Gln Ala Ala Arg Phe Phe Glu Ser Ala
        115                 120                 125 gaa gtt att gag ctg cac cac ccc aac aag ctg gat gca cct tca ggc     432
Glu Val Ile Glu Leu His His Pro Asn Lys Leu Asp Ala Pro Ser Gly
    130                 135                 140 acc gcg atc cac act gct cag ggc att gct gcg gca cgc aaa gaa gca     480
Thr Ala Ile His Thr Ala Gln Gly Ile Ala Ala Ala Arg Lys Glu Ala
145                 150                 155                 160 ggc atg gac gca cag cca gat gcg acc gag cag gca ctt gag ggt tcc     528
Gly Met Asp Ala Gln Pro Asp Ala Thr Glu Gln Ala Leu Glu Gly Ser
                165                 170                 175 cgt ggc gca agc gta gat gga atc cca gtt cac gca gtc cgc atg tcc     576
Arg Gly Ala Ser Val Asp Gly Ile Pro Val His Ala Val Arg Met Ser
            180                 185                 190 ggc atg gtt gct cac gag caa gtt atc ttt ggc acc cag ggt cag acc     624
Gly Met Val Ala His Glu Gln Val Ile Phe Gly Thr Gln Gly Gln Thr
        195                 200                 205 ttg acc atc aag cag gac tcc tat gat cgc aac tca ttt gca cca ggt     672
Leu Thr Ile Lys Gln Asp Ser Tyr Asp Arg Asn Ser Phe Ala Pro Gly
    210                 215                 220 gtc ttg gtg ggt gtg cgc aac att gca cag cac cca ggc cta gtc gta     720
Val Leu Val Gly Val Arg Asn Ile Ala Gln His Pro Gly Leu Val Val
225                 230                 235                 240 gga ctt gag cat tac cta ggc ctg taa                                 747
Gly Leu Glu His Tyr Leu Gly Leu
                245
```

<210> SEQ ID NO 6
<211> LENGTH: 248
<212> TYPE: PRT
<213> ORGANISM: Corynebacterium glutamicum

<400> SEQUENCE: 6

```
Met Gly Ile Lys Val Gly Val Leu Gly Ala Lys Gly Arg Val Gly Gln
1               5                   10                  15

Thr Ile Val Ala Ala Val Asn Glu Ser Asp Asp Leu Glu Leu Val Ala
            20                  25                  30

Glu Ile Gly Val Asp Asp Asp Leu Ser Leu Leu Val Asp Asn Gly Ala
```

```
                35                  40                  45
Glu Val Val Asp Phe Thr Thr Pro Asn Ala Val Met Gly Asn Leu
 50                  55                  60

Glu Phe Cys Ile Asn Asn Gly Ile Ser Ala Val Val Gly Thr Gly
 65                  70                  75                  80

Phe Asp Asn Ala Arg Leu Glu Gln Val Arg Ala Trp Leu Glu Gly Lys
                 85                  90                  95

Asp Asn Val Gly Val Leu Ile Ala Pro Asn Phe Ala Ile Ser Ala Val
                100                 105                 110

Leu Thr Met Val Phe Ser Lys Gln Ala Ala Arg Phe Phe Glu Ser Ala
                115                 120                 125

Glu Val Ile Glu Leu His His Pro Asn Lys Leu Asp Ala Pro Ser Gly
                130                 135                 140

Thr Ala Ile His Thr Ala Gln Gly Ile Ala Ala Ala Arg Lys Glu Ala
145                 150                 155                 160

Gly Met Asp Ala Gln Pro Asp Ala Thr Glu Gln Ala Leu Glu Gly Ser
                165                 170                 175

Arg Gly Ala Ser Val Asp Gly Ile Pro Val His Ala Val Arg Met Ser
                180                 185                 190

Gly Met Val Ala His Glu Gln Val Ile Phe Gly Thr Gln Gly Gln Thr
                195                 200                 205

Leu Thr Ile Lys Gln Asp Ser Tyr Asp Arg Asn Ser Phe Ala Pro Gly
                210                 215                 220

Val Leu Val Gly Val Arg Asn Ile Ala Gln His Pro Gly Leu Val Val
225                 230                 235                 240

Gly Leu Glu His Tyr Leu Gly Leu
                245

<210> SEQ ID NO 7
<211> LENGTH: 1023
<212> TYPE: DNA
<213> ORGANISM: Corynebacterium glutamicum
<220> FEATURE:
<221> NAME/KEY: CDS
<222> LOCATION: (1)..(1023)

<400> SEQUENCE: 7 atg cat ttc ggt aag ctc gac cag gac agt gcc acc aca att ttg gag    48
Met His Phe Gly Lys Leu Asp Gln Asp Ser Ala Thr Thr Ile Leu Glu
 1               5                  10                  15 gat tac aag aac atg acc aac atc cgc gta gct atc gta ggc tac gga    96
Asp Tyr Lys Asn Met Thr Asn Ile Arg Val Ala Ile Val Gly Tyr Gly
                 20                  25                  30 aac ctg gga cgc agc gtc gaa aag ctt att gcc aag cag ccc gac atg   144
Asn Leu Gly Arg Ser Val Glu Lys Leu Ile Ala Lys Gln Pro Asp Met
             35                  40                  45 gac ctt gta gga atc ttc tcg cgc cgg gcc acc ctc gac aca aag acg   192
Asp Leu Val Gly Ile Phe Ser Arg Arg Ala Thr Leu Asp Thr Lys Thr
 50                  55                  60 cca gtc ttt gat gtc gcc gac gtg gac aag cac gcc gac gac gtg gac   240
Pro Val Phe Asp Val Ala Asp Val Asp Lys His Ala Asp Asp Val Asp
 65                  70                  75                  80 gtg ctg ttc ctg tgc atg ggc tcc gcc acc gac atc cct gag cag gca   288
Val Leu Phe Leu Cys Met Gly Ser Ala Thr Asp Ile Pro Glu Gln Ala
                 85                  90                  95 cca aag ttc gcg cag ttc gcc tgc acc gta gac acc tac gac aac cac   336
Pro Lys Phe Ala Gln Phe Ala Cys Thr Val Asp Thr Tyr Asp Asn His
                100                 105                 110
```

```
cgc gac atc cca cgc cac cgc cag gtc atg aac gaa gcc gcc acc gca         384
Arg Asp Ile Pro Arg His Arg Gln Val Met Asn Glu Ala Ala Thr Ala
            115                 120                 125 gcc ggc aac gtt gca ctg gtc tct acc ggc tgg gat cca gga atg ttc         432
Ala Gly Asn Val Ala Leu Val Ser Thr Gly Trp Asp Pro Gly Met Phe
    130                 135                 140 tcc atc aac cgc gtc tac gca gcg gca gtc tta gcc gag cac cag cag         480
Ser Ile Asn Arg Val Tyr Ala Ala Ala Val Leu Ala Glu His Gln Gln
145                 150                 155                 160 cac acc ttc tgg ggc cca ggt ttg tca cag ggc cac tcc gat gct ttg         528
His Thr Phe Trp Gly Pro Gly Leu Ser Gln Gly His Ser Asp Ala Leu
                165                 170                 175 cga cgc atc cct ggc gtt caa aag gcc gtc cag tac acc ctc cca tcc         576
Arg Arg Ile Pro Gly Val Gln Lys Ala Val Gln Tyr Thr Leu Pro Ser
            180                 185                 190 gaa gaa gcc ctg gaa aag gcc cgc cgt ggc gaa gcc ggc gac ctc acc         624
Glu Glu Ala Leu Glu Lys Ala Arg Arg Gly Glu Ala Gly Asp Leu Thr
        195                 200                 205 gga aag caa acc cac aag cgc caa tgc ttc gtg gtt gcc gac gcg gcc         672
Gly Lys Gln Thr His Lys Arg Gln Cys Phe Val Val Ala Asp Ala Ala
    210                 215                 220 gac cac gag cgc atc gaa aac gac atc cgc acc atg cct gat tac ttc         720
Asp His Glu Arg Ile Glu Asn Asp Ile Arg Thr Met Pro Asp Tyr Phe
225                 230                 235                 240 gtt ggc tac gaa gtc gaa gtc aac ttc atc gac gaa gca acc ttg gac         768
Val Gly Tyr Glu Val Glu Val Asn Phe Ile Asp Glu Ala Thr Leu Asp
                245                 250                 255 gcc gag cac acc ggc atg cca cac ggc gga cac gtg atc acc acc ggc         816
Ala Glu His Thr Gly Met Pro His Gly Gly His Val Ile Thr Thr Gly
            260                 265                 270 gac acc ggt ggc ttc aac cac acc gtg gaa tac atc ctg aag ctg gac         864
Asp Thr Gly Gly Phe Asn His Thr Val Glu Tyr Ile Leu Lys Leu Asp
        275                 280                 285 cga aac cca gat ttc acc gct tct tca cag atc gct ttc ggc cgc gca         912
Arg Asn Pro Asp Phe Thr Ala Ser Ser Gln Ile Ala Phe Gly Arg Ala
    290                 295                 300 gct cac cgc atg aag cag cag ggc caa agc ggt gct ttc acc gtc ctc         960
Ala His Arg Met Lys Gln Gln Gly Gln Ser Gly Ala Phe Thr Val Leu
305                 310                 315                 320 gaa gtt gct cca tac ttg ctc tcc ccg gag aac ttg gat gat ctg atc        1008
Glu Val Ala Pro Tyr Leu Leu Ser Pro Glu Asn Leu Asp Asp Leu Ile
                325                 330                 335 gca cgc gac gtc taa                                                    1023
Ala Arg Asp Val
            340

<210> SEQ ID NO 8
<211> LENGTH: 340
<212> TYPE: PRT
<213> ORGANISM: Corynebacterium glutamicum

<400> SEQUENCE: 8

Met His Phe Gly Lys Leu Asp Gln Asp Ser Ala Thr Thr Ile Leu Glu
1               5                   10                  15

Asp Tyr Lys Asn Met Thr Asn Ile Arg Val Ala Ile Val Gly Tyr Gly
            20                  25                  30

Asn Leu Gly Arg Ser Val Glu Lys Leu Ile Ala Lys Gln Pro Asp Met
        35                  40                  45

Asp Leu Val Gly Ile Phe Ser Arg Arg Ala Thr Leu Asp Thr Lys Thr
    50                  55                  60
```

```
Pro Val Phe Asp Val Ala Asp Val Asp Lys His Ala Asp Asp Val Asp
65                  70                  75                  80

Val Leu Phe Leu Cys Met Gly Ser Ala Thr Asp Ile Pro Glu Gln Ala
                85                  90                  95

Pro Lys Phe Ala Gln Phe Ala Cys Thr Val Asp Thr Tyr Asp Asn His
            100                 105                 110

Arg Asp Ile Pro Arg His Arg Gln Val Met Asn Glu Ala Ala Thr Ala
        115                 120                 125

Ala Gly Asn Val Ala Leu Val Ser Thr Gly Trp Asp Pro Gly Met Phe
    130                 135                 140

Ser Ile Asn Arg Val Tyr Ala Ala Ala Val Leu Ala Glu His Gln Gln
145                 150                 155                 160

His Thr Phe Trp Gly Pro Gly Leu Ser Gln Gly His Ser Asp Ala Leu
                165                 170                 175

Arg Arg Ile Pro Gly Val Gln Lys Ala Val Gln Tyr Thr Leu Pro Ser
            180                 185                 190

Glu Glu Ala Leu Glu Lys Ala Arg Gly Glu Ala Gly Asp Leu Thr
        195                 200                 205

Gly Lys Gln Thr His Lys Arg Gln Cys Phe Val Val Ala Asp Ala Ala
    210                 215                 220

Asp His Glu Arg Ile Glu Asn Asp Ile Arg Thr Met Pro Asp Tyr Phe
225                 230                 235                 240

Val Gly Tyr Glu Val Glu Val Asn Phe Ile Asp Glu Ala Thr Leu Asp
                245                 250                 255

Ala Glu His Thr Gly Met Pro His Gly Gly His Val Ile Thr Thr Gly
            260                 265                 270

Asp Thr Gly Gly Phe Asn His Thr Val Glu Tyr Ile Leu Lys Leu Asp
        275                 280                 285

Arg Asn Pro Asp Phe Thr Ala Ser Ser Gln Ile Ala Phe Gly Arg Ala
    290                 295                 300

Ala His Arg Met Lys Gln Gln Gly Gln Ser Gly Ala Phe Thr Val Leu
305                 310                 315                 320

Glu Val Ala Pro Tyr Leu Leu Ser Pro Glu Asn Leu Asp Asp Leu Ile
                325                 330                 335

Ala Arg Asp Val
            340

<210> SEQ ID NO 9
<211> LENGTH: 753
<212> TYPE: DNA
<213> ORGANISM: Corynebacterium glutamicum
<220> FEATURE:
<221> NAME/KEY: CDS
<222> LOCATION: (1)..(753)

<400> SEQUENCE: 9 gtg gcc gaa caa gtt aaa ttg agc gtg gag ttg ata gcg tgc agt tct    48
Met Ala Glu Gln Val Lys Leu Ser Val Glu Leu Ile Ala Cys Ser Ser
1               5                   10                  15 ttt act cca ccc gct gat gtt gag tgg tca act gat gtt gag ggc gcg    96
Phe Thr Pro Pro Ala Asp Val Glu Trp Ser Thr Asp Val Glu Gly Ala
            20                  25                  30 gaa gca ctc gtc gag ttt gcg ggt cgt gcc tgc tac gaa act ttt gat   144
Glu Ala Leu Val Glu Phe Ala Gly Arg Ala Cys Tyr Glu Thr Phe Asp
        35                  40                  45 aag ccg aac cct cga act gct tcc aat gct gcg tat ctg cgc cac atc   192
Lys Pro Asn Pro Arg Thr Ala Ser Asn Ala Ala Tyr Leu Arg His Ile
    50                  55                  60
```

```
atg gaa gtg ggg cac act gct ttg ctt gag cat gcc aat gcc acg atg         240
Met Glu Val Gly His Thr Ala Leu Leu Glu His Ala Asn Ala Thr Met
 65                  70                  75                  80 tat atc cga ggc att tct cgg tcc gcg acc cat gaa ttg gtc cga cac         288
Tyr Ile Arg Gly Ile Ser Arg Ser Ala Thr His Glu Leu Val Arg His
                 85                  90                  95 cgc cat ttt tcc ttc tct caa ctg tct cag cgt ttc gtg cac agc gga         336
Arg His Phe Ser Phe Ser Gln Leu Ser Gln Arg Phe Val His Ser Gly
            100                 105                 110 gaa tcg gaa gta gtg gtg ccc act ctc atc gat gaa gat ccg cag ttg         384
Glu Ser Glu Val Val Val Pro Thr Leu Ile Asp Glu Asp Pro Gln Leu
        115                 120                 125 cgt gaa ctt ttc atg cac gcc atg gat gag tct cgg ttc gct ttc aat         432
Arg Glu Leu Phe Met His Ala Met Asp Glu Ser Arg Phe Ala Phe Asn
130                 135                 140 gag ctg ctt aat gcg ctg gaa gaa aaa ctt ggc gat gaa ccg aat gca         480
Glu Leu Leu Asn Ala Leu Glu Glu Lys Leu Gly Asp Glu Pro Asn Ala
145                 150                 155                 160 ctt tta agg aaa aag cag gct cgt caa gca gct cgc gct gtg ctg ccc         528
Leu Leu Arg Lys Lys Gln Ala Arg Gln Ala Ala Arg Ala Val Leu Pro
                165                 170                 175 aac gct aca gag tcc aga atc gtg gtg tct gga aac ttc cgc acc tgg         576
Asn Ala Thr Glu Ser Arg Ile Val Val Ser Gly Asn Phe Arg Thr Trp
            180                 185                 190 agg cat ttc att ggc atg cga gcc agt gaa cat gca gac gtc gaa atc         624
Arg His Phe Ile Gly Met Arg Ala Ser Glu His Ala Asp Val Glu Ile
        195                 200                 205 cgc gaa gta gcg gta gga tgt tta aga aag ctg cag gta gca gcg cca         672
Arg Glu Val Ala Val Gly Cys Leu Arg Lys Leu Gln Val Ala Ala Pro
210                 215                 220 act gtt ttc ggt gat ttt gag att gaa act ttg gca gac gga tcg caa         720
Thr Val Phe Gly Asp Phe Glu Ile Glu Thr Leu Ala Asp Gly Ser Gln
225                 230                 235                 240 atg gca aca agc ccg tat gtc atg gac ttt taa                             753
Met Ala Thr Ser Pro Tyr Val Met Asp Phe
                245                 250

<210> SEQ ID NO 10
<211> LENGTH: 250
<212> TYPE: PRT
<213> ORGANISM: Corynebacterium glutamicum

<400> SEQUENCE: 10

Met Ala Glu Gln Val Lys Leu Ser Val Glu Leu Ile Ala Cys Ser Ser
  1               5                  10                  15

Phe Thr Pro Pro Ala Asp Val Glu Trp Ser Thr Asp Val Glu Gly Ala
                 20                  25                  30

Glu Ala Leu Val Glu Phe Ala Gly Arg Ala Cys Tyr Glu Thr Phe Asp
            35                  40                  45

Lys Pro Asn Pro Arg Thr Ala Ser Asn Ala Ala Tyr Leu Arg His Ile
        50                  55                  60

Met Glu Val Gly His Thr Ala Leu Leu Glu His Ala Asn Ala Thr Met
 65                  70                  75                  80

Tyr Ile Arg Gly Ile Ser Arg Ser Ala Thr His Glu Leu Val Arg His
                 85                  90                  95

Arg His Phe Ser Phe Ser Gln Leu Ser Gln Arg Phe Val His Ser Gly
            100                 105                 110

Glu Ser Glu Val Val Val Pro Thr Leu Ile Asp Glu Asp Pro Gln Leu
        115                 120                 125
```

```
Arg Glu Leu Phe Met His Ala Met Asp Glu Ser Arg Phe Ala Phe Asn
        130                 135                 140

Glu Leu Leu Asn Ala Leu Glu Glu Lys Leu Gly Asp Glu Pro Asn Ala
145                 150                 155                 160

Leu Leu Arg Lys Lys Gln Ala Arg Gln Ala Ala Arg Ala Val Leu Pro
                165                 170                 175

Asn Ala Thr Glu Ser Arg Ile Val Val Ser Gly Asn Phe Arg Thr Trp
            180                 185                 190

Arg His Phe Ile Gly Met Arg Ala Ser Glu His Ala Asp Val Glu Ile
        195                 200                 205

Arg Glu Val Ala Val Gly Cys Leu Arg Lys Leu Gln Val Ala Ala Pro
    210                 215                 220

Thr Val Phe Gly Asp Phe Glu Ile Glu Thr Leu Ala Asp Gly Ser Gln
225                 230                 235                 240

Met Ala Thr Ser Pro Tyr Val Met Asp Phe
                245                 250
```

<210> SEQ ID NO 11
<211> LENGTH: 1338
<212> TYPE: DNA
<213> ORGANISM: Corynebacterium glutamicum
<220> FEATURE:
<221> NAME/KEY: CDS
<222> LOCATION: (1)..(1338)

<400> SEQUENCE: 11

```
atg gct aca gtt gaa aat ttc aat gaa ctt ccc gca cac gta tgg cca      48
Met Ala Thr Val Glu Asn Phe Asn Glu Leu Pro Ala His Val Trp Pro
1               5                   10                  15 cgc aat gcc gtg cgc caa gaa gac ggc gtt gtc acc gtc gct ggt gtg      96
Arg Asn Ala Val Arg Gln Glu Asp Gly Val Val Thr Val Ala Gly Val
            20                  25                  30 cct ctg cct gac ctc gct gaa gaa tac gga acc cca ctg ttc gta gtc     144
Pro Leu Pro Asp Leu Ala Glu Glu Tyr Gly Thr Pro Leu Phe Val Val
        35                  40                  45 gac gag gac gat ttc cgt tcc cgc tgt cgc gac atg gct acc gca ttc     192
Asp Glu Asp Asp Phe Arg Ser Arg Cys Arg Asp Met Ala Thr Ala Phe
    50                  55                  60 ggt gga cca ggc aat gtg cac tac gca tct aaa gcg ttc ctg acc aag     240
Gly Gly Pro Gly Asn Val His Tyr Ala Ser Lys Ala Phe Leu Thr Lys
65                  70                  75                  80 acc att gca cgt tgg gtt gat gaa gag ggg ctg gca ctg gac att gca     288
Thr Ile Ala Arg Trp Val Asp Glu Glu Gly Leu Ala Leu Asp Ile Ala
                85                  90                  95 tcc atc aac gaa ctg ggc att gcc ctg gcc gct ggt ttc ccc gcc agc     336
Ser Ile Asn Glu Leu Gly Ile Ala Leu Ala Ala Gly Phe Pro Ala Ser
            100                 105                 110 cgt atc acc gcg cac ggc aac aac aaa ggc gta gag ttc ctg cgc gcg     384
Arg Ile Thr Ala His Gly Asn Asn Lys Gly Val Glu Phe Leu Arg Ala
        115                 120                 125 ttg gtt caa aac ggt gtg gga cac gtg gtg ctg gac tcc gca cag gaa     432
Leu Val Gln Asn Gly Val Gly His Val Val Leu Asp Ser Ala Gln Glu
    130                 135                 140 cta gaa ctg ttg gat tac gtt gcc gct ggt gaa ggc aag att cag gac     480
Leu Glu Leu Leu Asp Tyr Val Ala Ala Gly Glu Gly Lys Ile Gln Asp
145                 150                 155                 160 gtg ttg atc cgc gta aag cca ggc atc gaa gca cac acc cac gag ttc     528
Val Leu Ile Arg Val Lys Pro Gly Ile Glu Ala His Thr His Glu Phe
                165                 170                 175
```

```
atc gcc act agc cac gaa gac cag aag ttc gga ttc tcc ctg gca tcc      576
Ile Ala Thr Ser His Glu Asp Gln Lys Phe Gly Phe Ser Leu Ala Ser
            180                 185                 190 ggt tcc gca ttc gaa gca gca aaa gcc gcc aac aac gca gaa aac ctg      624
Gly Ser Ala Phe Glu Ala Ala Lys Ala Ala Asn Asn Ala Glu Asn Leu
        195                 200                 205 aac ctg gtt ggc ctg cac tgc cac gtt ggt tcc cag gtg ttc gac gcc      672
Asn Leu Val Gly Leu His Cys His Val Gly Ser Gln Val Phe Asp Ala
    210                 215                 220 gaa ggc ttc aag ctg gca gca gaa cgc gtg ttg ggc ctg tac tca cag      720
Glu Gly Phe Lys Leu Ala Ala Glu Arg Val Leu Gly Leu Tyr Ser Gln
225                 230                 235                 240 atc cac agc gaa ctg ggc gtt gcc ctt cct gaa ctg gat ctc ggt ggc      768
Ile His Ser Glu Leu Gly Val Ala Leu Pro Glu Leu Asp Leu Gly Gly
                245                 250                 255 gga tac ggc att gcc tat acc gca gct gaa gaa cca ctc aac gtc gca      816
Gly Tyr Gly Ile Ala Tyr Thr Ala Ala Glu Glu Pro Leu Asn Val Ala
            260                 265                 270 gaa gtt gcc tcc gac ctg ctc acc gca gtc gga aaa atg gca gcg gaa      864
Glu Val Ala Ser Asp Leu Leu Thr Ala Val Gly Lys Met Ala Ala Glu
        275                 280                 285 cta ggc atc gac gca cca acc gtg ctt gtt gag ccc ggc cgc gct atc      912
Leu Gly Ile Asp Ala Pro Thr Val Leu Val Glu Pro Gly Arg Ala Ile
    290                 295                 300 gca ggc ccc tcc acc gtg acc atc tac gaa gtc ggc acc acc aaa gac      960
Ala Gly Pro Ser Thr Val Thr Ile Tyr Glu Val Gly Thr Thr Lys Asp
305                 310                 315                 320 gtc cac gta gac gac gac aaa acc cgc cgt tac atc gcc gtg gac gga     1008
Val His Val Asp Asp Asp Lys Thr Arg Arg Tyr Ile Ala Val Asp Gly
                325                 330                 335 ggc atg tcc gac aac atc cgc cca gca ctc tac ggc tcc gaa tac gac     1056
Gly Met Ser Asp Asn Ile Arg Pro Ala Leu Tyr Gly Ser Glu Tyr Asp
            340                 345                 350 gcc cgc gta gta tcc cgc ttc gcc gaa gga gac cca gta agc acc cgc     1104
Ala Arg Val Val Ser Arg Phe Ala Glu Gly Asp Pro Val Ser Thr Arg
        355                 360                 365 atc gtg ggc tcc cac tgc gaa tcc ggc gat atc ctg atc aac gat gaa     1152
Ile Val Gly Ser His Cys Glu Ser Gly Asp Ile Leu Ile Asn Asp Glu
    370                 375                 380 atc tac cca tct gac atc acc agc ggc gac ttc ctt gca ctc gca gcc     1200
Ile Tyr Pro Ser Asp Ile Thr Ser Gly Asp Phe Leu Ala Leu Ala Ala
385                 390                 395                 400 acc ggc gca tac tgc tac gcc atg agc tcc cgc tac aac gcc ttc aca     1248
Thr Gly Ala Tyr Cys Tyr Ala Met Ser Ser Arg Tyr Asn Ala Phe Thr
                405                 410                 415 cgg ccc gcc gtc gtg tcc gtc cgc gct ggc agc tcc cgc ctc atg ctg     1296
Arg Pro Ala Val Val Ser Val Arg Ala Gly Ser Ser Arg Leu Met Leu
            420                 425                 430 cgc cgc gaa acg ctc gac gac atc ctc tca cta gag gca taa             1338
Arg Arg Glu Thr Leu Asp Asp Ile Leu Ser Leu Glu Ala
        435                 440                 445

<210> SEQ ID NO 12
<211> LENGTH: 445
<212> TYPE: PRT
<213> ORGANISM: Corynebacterium glutamicum

<400> SEQUENCE: 12

Met Ala Thr Val Glu Asn Phe Asn Glu Leu Pro Ala His Val Trp Pro
1               5                   10                  15

Arg Asn Ala Val Arg Gln Glu Asp Gly Val Val Thr Val Ala Gly Val
```

```
                20                  25                  30
Pro Leu Pro Asp Leu Ala Glu Glu Tyr Gly Thr Pro Leu Phe Val Val
            35                  40                  45

Asp Glu Asp Asp Phe Arg Ser Arg Cys Arg Asp Met Ala Thr Ala Phe
50                  55                  60

Gly Gly Pro Gly Asn Val His Tyr Ala Ser Lys Ala Phe Leu Thr Lys
65                  70                  75                  80

Thr Ile Ala Arg Trp Val Asp Glu Gly Leu Ala Leu Asp Ile Ala
                85                  90                  95

Ser Ile Asn Glu Leu Gly Ile Ala Leu Ala Ala Gly Phe Pro Ala Ser
            100                 105                 110

Arg Ile Thr Ala His Gly Asn Asn Lys Gly Val Glu Phe Leu Arg Ala
            115                 120                 125

Leu Val Gln Asn Gly Val Gly His Val Val Leu Asp Ser Ala Gln Glu
            130                 135                 140

Leu Glu Leu Leu Asp Tyr Val Ala Ala Gly Gly Lys Ile Gln Asp
145                 150                 155                 160

Val Leu Ile Arg Val Lys Pro Gly Ile Glu Ala His Thr His Glu Phe
                165                 170                 175

Ile Ala Thr Ser His Glu Asp Gln Lys Phe Gly Phe Ser Leu Ala Ser
            180                 185                 190

Gly Ser Ala Phe Glu Ala Ala Lys Ala Ala Asn Asn Ala Glu Asn Leu
            195                 200                 205

Asn Leu Val Gly Leu His Cys His Val Gly Ser Gln Val Phe Asp Ala
            210                 215                 220

Glu Gly Phe Lys Leu Ala Ala Glu Arg Val Leu Gly Leu Tyr Ser Gln
225                 230                 235                 240

Ile His Ser Glu Leu Gly Val Ala Leu Pro Glu Leu Asp Leu Gly Gly
                245                 250                 255

Gly Tyr Gly Ile Ala Tyr Thr Ala Ala Glu Glu Pro Leu Asn Val Ala
            260                 265                 270

Glu Val Ala Ser Asp Leu Leu Thr Ala Val Gly Lys Met Ala Ala Glu
            275                 280                 285

Leu Gly Ile Asp Ala Pro Thr Val Leu Val Glu Pro Gly Arg Ala Ile
            290                 295                 300

Ala Gly Pro Ser Thr Val Thr Ile Tyr Glu Val Gly Thr Thr Lys Asp
305                 310                 315                 320

Val His Val Asp Asp Lys Thr Arg Arg Tyr Ile Ala Val Asp Gly
                325                 330                 335

Gly Met Ser Asp Asn Ile Arg Pro Ala Leu Tyr Gly Ser Glu Tyr Asp
            340                 345                 350

Ala Arg Val Val Ser Arg Phe Ala Glu Gly Asp Pro Val Ser Thr Arg
            355                 360                 365

Ile Val Gly Ser His Cys Glu Ser Gly Asp Ile Leu Ile Asn Asp Glu
            370                 375                 380

Ile Tyr Pro Ser Asp Ile Thr Ser Gly Asp Phe Leu Ala Leu Ala Ala
385                 390                 395                 400

Thr Gly Ala Tyr Cys Tyr Ala Met Ser Ser Arg Tyr Asn Ala Phe Thr
                405                 410                 415

Arg Pro Ala Val Val Ser Val Arg Ala Gly Ser Ser Arg Leu Met Leu
            420                 425                 430

Arg Arg Glu Thr Leu Asp Asp Ile Leu Ser Leu Glu Ala
            435                 440                 445
```

<210> SEQ ID NO 13
<211> LENGTH: 365
<212> TYPE: DNA
<213> ORGANISM: Corynebacterium glutamicum
<220> FEATURE:
<221> NAME/KEY: CDS
<222> LOCATION: (1)..(365)

<400> SEQUENCE: 13

```
gtg gcc gaa caa gtt aaa ttg agc gtg gag ttg ata gcg tgc agt tct      48
Met Ala Glu Gln Val Lys Leu Ser Val Glu Leu Ile Ala Cys Ser Ser
1               5                   10                  15 ttt act cca ccc gct gat gtt gag tgg tca act gat gtt gag ggc gcg      96
Phe Thr Pro Pro Ala Asp Val Glu Trp Ser Thr Asp Val Glu Gly Ala
            20                  25                  30 gaa gca ctc gtc gag ttt gcg ggt cgt gcc tgc tac gaa act ttt gat     144
Glu Ala Leu Val Glu Phe Ala Gly Arg Ala Cys Tyr Glu Thr Phe Asp
        35                  40                  45 aag ccg aac cct cga act gct tcc aat gct gcg tat ctg cgc cac atc     192
Lys Pro Asn Pro Arg Thr Ala Ser Asn Ala Ala Tyr Leu Arg His Ile
    50                  55                  60 atg gaa gtg ggg cac act gct ttg ctt gag cat gcc aat gcc acg atg     240
Met Glu Val Gly His Thr Ala Leu Leu Glu His Ala Asn Ala Thr Met
65                  70                  75                  80 tat atc cga ggc att tct cgg tcc gcg acc cat gaa ttg gtc cga cac     288
Tyr Ile Arg Gly Ile Ser Arg Ser Ala Thr His Glu Leu Val Arg His
                85                  90                  95 cgc cat ttt tcc ttc tct caa ctg tct cag cgt ttc gtg cac agc gga     336
Arg His Phe Ser Phe Ser Gln Leu Ser Gln Arg Phe Val His Ser Gly
            100                 105                 110 gaa tcg gaa gta gtg gtg ccc act ctc at                              365
Glu Ser Glu Val Val Val Pro Thr Leu Ile
        115                 120
```

<210> SEQ ID NO 14
<211> LENGTH: 122
<212> TYPE: PRT
<213> ORGANISM: Corynebacterium glutamicum

<400> SEQUENCE: 14

```
Met Ala Glu Gln Val Lys Leu Ser Val Glu Leu Ile Ala Cys Ser Ser
1               5                   10                  15

Phe Thr Pro Pro Ala Asp Val Glu Trp Ser Thr Asp Val Glu Gly Ala
            20                  25                  30

Glu Ala Leu Val Glu Phe Ala Gly Arg Ala Cys Tyr Glu Thr Phe Asp
        35                  40                  45

Lys Pro Asn Pro Arg Thr Ala Ser Asn Ala Ala Tyr Leu Arg His Ile
    50                  55                  60

Met Glu Val Gly His Thr Ala Leu Leu Glu His Ala Asn Ala Thr Met
65                  70                  75                  80

Tyr Ile Arg Gly Ile Ser Arg Ser Ala Thr His Glu Leu Val Arg His
                85                  90                  95

Arg His Phe Ser Phe Ser Gln Leu Ser Gln Arg Phe Val His Ser Gly
            100                 105                 110

Glu Ser Glu Val Val Val Pro Thr Leu Ile
        115                 120
```

<210> SEQ ID NO 15
<211> LENGTH: 551
<212> TYPE: DNA
<213> ORGANISM: Corynebacterium glutamicum -continued

```
<400> SEQUENCE: 15
aaccggtgtg gagccgacca ttccgcgagg ctgcactgca acgaggtcgt agttttggta        60
catggcttct ggccagttca tggattggct gccgaagaag ctataggcat cgccaccagg       120
gccaccggag ttaccgaaga tggtgccgtg cttttcgcct gggcaggga ccttgacaaa        180 gcccacgctg atatcgccaa gtgagggatc agaatagtgc atgggcacgt cgatgctgcc       240
acattgagcg gaggcaatat ctacctgagg tgggcattct tcccagcgga tgttttcttg       300
cgctgctgca gtgggcattg ataccaaaaa ggggctaagc gcagtcgagg cggcaagaac       360
tgctactacc ttttttattg tcgaacgggg cattacggct ccaaggacgt ttgttttctg       420
ggtcagttac cccaaaaagc atatacagag accaatgatt tttcattaaa aaggcaggga       480
tttgttataa gtatgggtcg tattctgtgc gacgggtgta cctcggctag aatttctccc       540
catgacacca g                                                            551

<210> SEQ ID NO 16
<211> LENGTH: 421
<212> TYPE: PRT
<213> ORGANISM: Artificial Sequence
<220> FEATURE:
<223> OTHER INFORMATION: Consensus Sequence of Protein Sequence
      Alignment
<220> FEATURE:
<221> NAME/KEY: MISC_FEATURE
<222> LOCATION: (40)..(40)
<223> OTHER INFORMATION: May be either Cys or Val
<220> FEATURE:
<221> NAME/KEY: MISC_FEATURE
<222> LOCATION: (317)..(317)
<223> OTHER INFORMATION: May be either Ser or Ala
<220> FEATURE:
<221> NAME/KEY: MISC_FEATURE
<222> LOCATION: (345)..(345)
<223> OTHER INFORMATION: May be either Gly or Asp
<220> FEATURE:
<221> NAME/KEY: MISC_FEATURE
<222> LOCATION: (380)..(380)
<223> OTHER INFORMATION: May be either Thr or Ile

<400> SEQUENCE: 16

Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Val Xaa Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160
```

```
Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
    290                 295                 300

Asp Gly Thr Thr Asp Ile Thr Phe Thr Cys Pro Arg Xaa Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Xaa Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Xaa Ser Glu Ile Arg
    370                 375                 380

Ile Ser Val Leu Ile Arg Glu Asp Asp Leu Asp Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420

<210> SEQ ID NO 17
<211> LENGTH: 28
<212> TYPE: DNA
<213> ORGANISM: Artificial Sequence
<220> FEATURE:
<223> OTHER INFORMATION: Primer

<400> SEQUENCE: 17
gggtacctcg cgaagtagca cctgtcac                                        28

<210> SEQ ID NO 18
<211> LENGTH: 26
<212> TYPE: DNA
<213> ORGANISM: Artificial Sequence
<220> FEATURE:
<223> OTHER INFORMATION: Primer

<400> SEQUENCE: 18
gcggatcccc catcgcccct caaaga                                          26

<210> SEQ ID NO 19
<211> LENGTH: 21
<212> TYPE: DNA
<213> ORGANISM: Artificial Sequence
```

```
<220> FEATURE:
<223> OTHER INFORMATION: Primer

<400> SEQUENCE: 19
aacgggcggt gaagggcaac t                                          21

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
tgaaagacag gggtatccag a                                          21

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
ccatggtacc aagtgcgtgg cgag                                       24

<210> SEQ ID NO 22
<211> LENGTH: 25
<212> TYPE: DNA
<213> ORGANISM: Artificial Sequence
<220> FEATURE:
<223> OTHER INFORMATION: Primer

<400> SEQUENCE: 22
ccatggtacc acactgtttc cttgc                                      25

<210> SEQ ID NO 23
<211> LENGTH: 25
<212> TYPE: DNA
<213> ORGANISM: Artificial Sequence
<220> FEATURE:
<223> OTHER INFORMATION: Primer

<400> SEQUENCE: 23
ccggagaaga tgtaacaatg gctac                                      25

<210> SEQ ID NO 24
<211> LENGTH: 25
<212> TYPE: DNA
<213> ORGANISM: Artificial Sequence
<220> FEATURE:
<223> OTHER INFORMATION: Primer

<400> SEQUENCE: 24
cctcgactgc agaccctag acacc                                       25

<210> SEQ ID NO 25
<211> LENGTH: 30
<212> TYPE: DNA
<213> ORGANISM: Artificial Sequence
<220> FEATURE:
<223> OTHER INFORMATION: Primer

<400> SEQUENCE: 25
gctcatagag ttcaaggtta ccttcttccc                                 30
```

What is claimed is:
1. A vector selected from the group consisting of pDElia2$_{FC5}$-KDB, pK184-KDBH, pDElia2$_{FC5}$-KDB2, and pDElia2$_{FC5}$-KDB2HP1L.

* * * * *